(12) United States Patent
Perryman et al.

(10) Patent No.: US 11,672,488 B1
(45) Date of Patent: *Jun. 13, 2023

(54) PULSE-DENSITY MODULATION TO SYNTHESIZE STIMULATION WAVEFORMS ON AN IMPLANTABLE DEVICE

(71) Applicant: Stimwave Technologies Incorporated, Pompano Beach, FL (US)

(72) Inventors: Laura Tyler Perryman, Pompano Beach, FL (US); Bertan Bakkaloglu, Scottsdale, AZ (US); Chad David Andresen, Miami Beach, FL (US)

(73) Assignee: Stimwave Technologies Incorporated, Pompano Beach, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/855,252

(22) Filed: Apr. 22, 2020

Related U.S. Application Data

(63) Continuation of application No. 15/604,313, filed on May 24, 2017, now Pat. No. 10,646,164.
(Continued)

(51) Int. Cl.
*A61N 1/36* (2006.01)
*A61B 5/00* (2006.01)
*A61N 1/39* (2006.01)

(52) U.S. Cl.
CPC .............. *A61B 5/72* (2013.01); *A61B 5/0004* (2013.01); *A61N 1/3606* (2013.01); *A61N 1/36071* (2013.01); *A61N 1/395* (2013.01)

(58) Field of Classification Search
CPC ........................ A61N 1/3787; A61N 1/36189
See application file for complete search history.

(56) References Cited

U.S. PATENT DOCUMENTS

| 4,592,359 | A | * | 6/1986 | Galbraith | ........... A61N 1/36038 607/57 |
| 6,415,181 | B1 | * | 7/2002 | Schu | ...................... A61N 1/372 607/16 |

(Continued)

FOREIGN PATENT DOCUMENTS

| WO | WO 2012103519 | 8/2012 |
| WO | WO 2012138782 | 10/2012 |

(Continued)

*Primary Examiner* — George R Evanisko
(74) *Attorney, Agent, or Firm* — Fish & Richardson P.C.

(57) ABSTRACT

A wirelessly powered implantable stimulator device includes one or more antenna configured to receive an input signal non-inductively from an external antenna, the input signal containing (i) electrical energy to operate the implantable stimulator device and (ii) configuration data according to which a pulse-density modulation (PDM) encoded stimulus waveform signal is retrieved to synthesize a desired stimulation waveform; a circuit coupled to the one or more antenna; and one or more electrodes coupled to the circuit and configured to apply the desired stimulation waveform to neural tissue, wherein the circuit is configured to: rectify the input signal received at the one or more antennas non-inductively; extract the electrical energy and the configuration data from the input signal; and in accordance with the extracted configuration data, retrieve the pulse-density modulation (PDM) signal to synthesize the desired stimulation waveform therefrom.

9 Claims, 13 Drawing Sheets

Related U.S. Application Data

(60) Provisional application No. 62/340,580, filed on May 24, 2016.

(56) References Cited

U.S. PATENT DOCUMENTS

| | | | |
|---|---|---|---|
| 7,191,014 | B2 | 3/2007 | Kobayashi |
| 9,427,584 | B2 * | 8/2016 | Kaula ................ A61N 1/3606 |
| 9,782,587 | B2 | 10/2017 | Trier et al. |
| 10,646,164 | B1 * | 5/2020 | Perryman ............ A61N 1/3787 |
| 2006/0239482 | A1 * | 10/2006 | Hatoum ............. A61N 1/37229 |
| | | | 381/312 |
| 2007/0078498 | A1 | 4/2007 | Rezai et al. |
| 2012/0022613 | A1 * | 1/2012 | Meskens ................ H02J 7/025 |
| | | | 607/57 |
| 2016/0008602 | A1 | 1/2016 | Perryman et al. |

FOREIGN PATENT DOCUMENTS

| | | |
|---|---|---|
| WO | WO 2013019757 | 2/2013 |
| WO | WO 2013025632 | 2/2013 |
| WO | WO 2013040549 | 3/2013 |

* cited by examiner

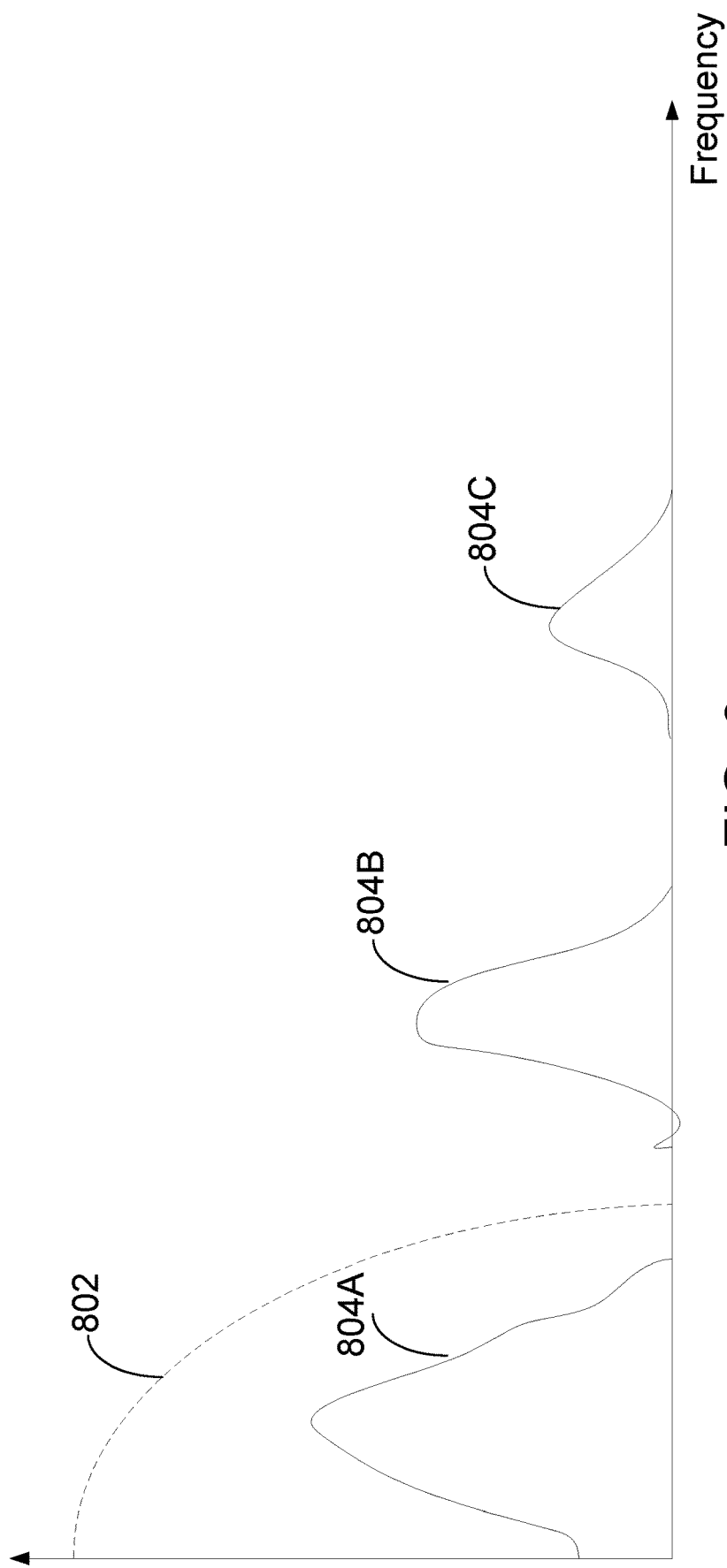

PULSE-DENSITY MODULATION TO SYNTHESIZE STIMULATION WAVEFORMS ON AN IMPLANTABLE DEVICE

CROSS-REFERENCE TO RELATED APPLICATIONS

This application is a continuation of U.S. application Ser. No. 15/604,313, filed May 24, 2017, now allowed, which claims the benefit of U.S. Provisional Application No. 62/340,580, filed May 24, 2016, and titled "Pulse-Density Modulation to Synthesize Stimulation Waveforms on an Implantable Device." Both of these prior applications are incorporated by reference in their entirety.

TECHNICAL FIELD

This application relates generally to implantable stimulators.

BACKGROUND

Modulation of excitable tissue in the body by electrical stimulation has become an important type of therapy for patients with chronic disabling conditions, including chronic pain, problems of movement initiation and control, involuntary movements, vascular insufficiency, heart arrhythmias and more. A variety of therapeutic intra-body electrical stimulation techniques can treat these conditions. For instance, devices may be used to deliver stimulatory signals to excitable tissue, record vital signs, perform pacing or defibrillation operations, record action potential activity from targeted tissue, control drug release from time-release capsules or drug pump units, or interface with the auditory system to assist with hearing. Typically, such devices utilize a subcutaneous battery operated implantable pulse generator (IPG) to provide power or other charge storage mechanisms.

SUMMARY

In one aspect, some implementations provide a wirelessly powered implantable stimulator device that includes: one or more antenna configured to receive an input signal through non-inductively coupling from an external antenna on an external controller, the input signal containing (i) electrical energy to operate the implantable stimulator device and (ii) configuration data according to which a pulse-density modulation (PDM) encoded stimulus waveform signal is retrieved to synthesize a desired stimulation waveform; a circuit coupled to the one or more antenna of the wirelessly powered implantable stimulator device; and one or more electrodes coupled to the circuit and configured to apply the desired stimulation waveform to neural tissue, wherein the circuit is configured to: rectify the input signal received at the one or more antennas non-inductively from the external controller; extract the electrical energy and the configuration data from the input signal; and in accordance with the extracted configuration data, retrieve the pulse-density modulation (PDM) signal to synthesize the desired stimulation waveform therefrom.

Implementations may include one of more of the following features.

The circuit may include a memory device on which the PDM encoded stimulus waveform signal is stored. The memory device may include a read-only memory device pre-loaded with the PDM encoded stimulus waveform signal that is tuned to treating a particular condition for a subject. The memory device may store the PDM encoded stimulus waveform signal as a bit stream such that the desired stimulation waveform is synthesized at least in part by serially shifting out the bit stream. The wirelessly powered implantable stimulator device may further include a multiplexing device, wherein the circuit may include more than one memory devices, each configured to store a PDM encoded stimulus waveform signal; and wherein the multiplexing device may be configured to select a particular PDM encoded stimulus waveform signal from one of the memory devices.

The circuit may include an integrate-and-hold component configured to demodulate the retrieved PDM encoded stimulus waveform signal such that the desired simulation waveform is synthesized by solely drawing on the extracted electrical energy. The configuration data may include polarity information and wherein the circuit is configured to set polarity state for each electrode in accordance with the polarity information. The configuration data may include information encoding a pulse duration and a repetition rate, and wherein the PDM encoded stimulus waveform signal is capable of synthesis into the desired stimulation waveform according to the pulse duration and the repetition rate. The wirelessly powered implantable stimulator device may further include a clock device coupled to the memory device and configured to speed up data output from the memory device when the pulse duration is reduced and slow down data output from the memory device when the pulse duration is increased.

The configuration data may include information encoding an amplitude, and wherein the desired stimulation waveform may be synthesized according to the amplitude.

The wirelessly powered implantable stimulator device may further include a sensor device coupled to the one or more electrodes, the sensor device configured to sense and integrate a direct current (DC) offset across neural tissue where the one or more electrodes have been implanted to apply the desired stimulation waveform. The wirelessly powered implantable stimulator device may further include a full bridge PDM driver coupled to each electrode, and wherein the sensor device is coupled to the full bridge PDM driver and further configured to drive the full bridge PDM driver using information of the DC offset sensed and integrated. The sensor device comprises a DC servo loop coupled to the full bridge PDM driver and the one or more electrodes.

The wirelessly powered implantable stimulator device may further include: a single-bit driver coupled to each electrode.

In another aspect, some implementations provide a method to synthesize a desired stimulation waveform for stimulating neural tissue, the method including: accessing information representing the desired stimulation waveform; generating a pulse-density modulation (PDM) encoded stimulus waveform signal representing the desired stimulation waveform by modulating the desired stimulation waveform; and storing the PDM encoded stimulus waveform signal in a memory device on an implantable stimulation device such that the desired stimulation waveform is synthesized from the encoded stimulus waveform signal in accordance with configuration data contained in an input signal received non-inductively at the implantable stimulation device, the input signal further containing electrical energy to operate the implantable stimulator device such that the desired stimulation waveform is synthesized by drawing on the electrical energy alone.

Some implementations may include one or more of the following features.

Generating the PDM encoded stimulus waveform signal by modulating the desired stimulation waveform may include: oversampling the desired stimulation waveform according to an oversampling ratio. The configuration data may include a pulse duration parameter, and wherein the desired stimulation waveform may be synthesized from the bit stream by clocking the bit stream faster when the pulse duration parameter is reduced and clocking the bit stream slower when the pulse duration parameter is increased such that the oversampling ratio is maintained.

Generating a pulse-density modulation (PDM) encoded stimulus waveform signal may include: generating a bitstream representing the desired stimulation waveform. The desired stimulation waveform signal may be tuned to treating a particular condition for a subject. Storing the PDM encoded stimulus waveform signal in a memory device may include storing the PDM encoded stimulus waveform signal in a read-only memory device.

Various implementations may be inherently low in cost compared to existing implantable neural modulation systems, and this may lead to wider adoption of neural modulation therapy for patients in need as well as reduction in overall cost to the healthcare system.

The details of one or more implementations are set forth in the accompanying drawings and the description below. Other features, objects, and advantages will be apparent from the description and drawings, and from the claims.

BRIEF DESCRIPTION OF THE DRAWINGS

FIG. 8 shows an example of a spectrum of a PDM waveform.

Like reference symbols in the various drawings indicate like elements.

DETAILED DESCRIPTION

Figure 1:
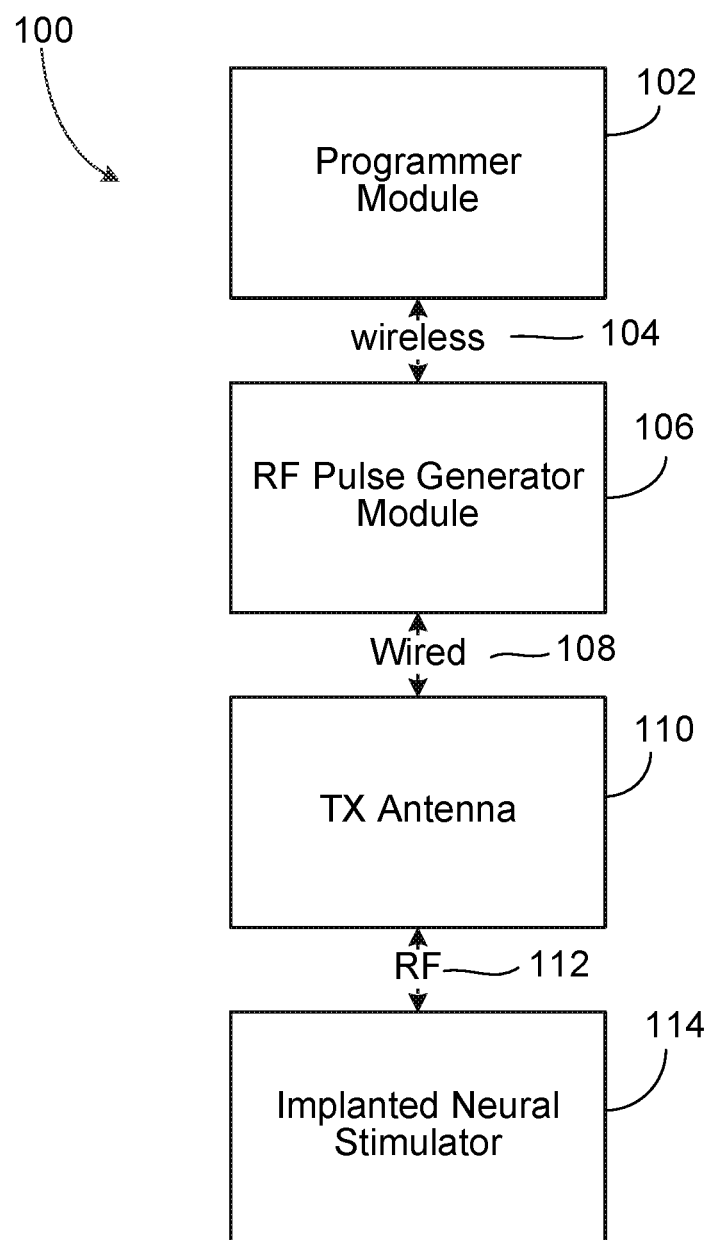
FIG. 1 depicts a high-level diagram of an example of a wireless stimulation system.

In various implementations, systems and methods are disclosed for applying one or more electrical impulses to targeted excitable tissue, such as nerves, for treating chronic pain, inflammation, arthritis, sleep apnea, seizures, incontinence, pain associated with cancer, incontinence, problems of movement initiation and control, involuntary movements, vascular insufficiency, heart arrhythmias, obesity, diabetes, craniofacial pain, such as migraines or cluster headaches, and other disorders. In certain embodiments, a device may be used to send electrical energy to targeted nerve tissue by using remote radio frequency (RF) energy without cables or inductive coupling to power a passive implanted wireless stimulator device. The targeted nerves can include, but are not limited to, the spinal cord and surrounding areas, including the dorsal horn, dorsal root ganglion, the exiting nerve roots, nerve ganglions, the dorsal column fibers and the peripheral nerve bundles leaving the dorsal column and brain, such as the vagus, occipital, trigeminal, hypoglossal, sacral, coccygeal nerves and the like.

A wireless stimulation system can include an implantable stimulator device with one or more electrodes and one or more conductive antennas (for example, dipole or patch antennas), and internal circuitry for frequency waveform and electrical energy rectification. The system may further comprise an external controller and antenna for transmitting radio frequency or microwave energy from an external source to the implantable stimulator device with neither cables nor inductive coupling to provide power.

In various implementations, the wireless implantable stimulator device is powered wirelessly (and therefore does not require a wired connection) and contains the circuitry necessary to receive the pulse instructions from a source external to the body. For example, various embodiments employ internal dipole (or other) antenna configuration(s) to receive RF power through electrical radiative coupling. This allows such devices to produce electrical currents capable of stimulating nerve bundles without a physical connection to an implantable pulse generator (IPG) or use of an inductive coil.

In some implementations, the wireless implantable stimulator device includes an application-specific integrated circuit (ASIC) chip for interacting with an external controller and the electrodes contained within the device. The ASIC chip may harvest RF power from the received input signal sent from the external controller to power the wireless implantable stimulator device, including the ASIC chip. The ASIC chip may also extract waveform parameters from the received input signal and use such information to create electrical impulses for stimulating excitable tissues through the electrodes. A pulse-density modulation (PDM) may be utilized to synthesize stimulation waveforms suitable for stimulating neural tissue. In some instances, an arbitrary waveform shape is created irrespective of the underlying tissue characteristics. In these instances, the arbitrary waveform shape is created consistently in a repeatable manner by leveraging the band-pass spectral characteristic of analog circuits driving the electrodes as well as the capacitive nature of tissue impedance. In one example, the stimulation waveform is constructed based on a single-bit representation that encodes the amplitude information. In this example, the amplitude information may be encoded in the lower spectral region. In addition, the ASIC chip contains a current steering feature to mirror currents to each electrode with evenness while maintaining a compact chip size. Moreover, the ASIC chip may extract polarity setting information from the received input signal and use such information to set the polarity for electrode interfaces.

Further descriptions of exemplary wireless systems for providing neural stimulation to a patient can be found in commonly-assigned, co-pending published PCT and US applications PCT/US2012/23029 filed Jan. 28, 2011, PCT/US2012/32200 filed Apr. 11, 2011, PCT/US2012/48903, filed Jan. 28, 2011, PCT/US2012/50633, filed Aug. 12, 2011, and PCT/US2012/55746, filed Sep. 15, 2011, US2016/

0008602 filed Jul. 19, 2015, the complete disclosures of which are incorporated by reference.

FIG. 1 depicts a high-level diagram of an example of a wireless stimulation system. The wireless stimulation system may include four major components, namely, a programmer module 102, a RF pulse generator module 106, a transmit (TX) antenna 110 (for example, a patch antenna, slot antenna, or a dipole antenna), and an implanted wireless stimulator device 114. The programmer module 102 may be a computer device, such as a smart phone, running a software application that supports a wireless connection 104, such as Bluetooth®. The application can enable the user to view the system status and diagnostics, change various parameters, increase/decrease the desired stimulus amplitude of the electrode pulses, and adjust feedback sensitivity of the RF pulse generator module 106, among other functions.

The RF pulse generator module 106 may include communication electronics that support the wireless connection 104, the stimulation circuitry, and the battery to power the generator electronics. In some implementations, the RF pulse generator module 106 includes the TX antenna embedded into its packaging form factor while, in other implementations, the TX antenna is connected to the RF pulse generator module 106 through a wired connection 108 or a wireless connection (not shown). The TX antenna 110 may be coupled directly to tissue to create an electric field that powers the implanted wireless stimulator device 114. The TX antenna 110 communicates with the implanted wireless stimulator device 114 through an RF interface. For instance, the TX antenna 110 radiates an RF transmission signal that is modulated and encoded by the RF pulse generator module 110. The implanted wireless stimulator device of module 114 contains one or more antennas, such as dipole antenna(s), to receive and transmit through RF interface 112. In particular, the coupling mechanism between antenna 110 and the one or more antennas on the implanted wireless stimulation device of module 114 utilizes electrical radiative coupling and not inductive coupling. In other words, the coupling is through an electric field rather than a magnetic field.

Through this electromagnetic radiative coupling, the TX antenna 110 can provide an input signal to the implanted wireless stimulator device 114. Within the implanted wireless stimulator device 114 are components for demodulating the RF transmission signal, and electrodes to deliver the stimulation to surrounding neuronal tissue. The input signal contains electrical energy to power the creation of a stimulation waveform so that the stimulation waveform can be synthesized and applied at the electrodes. The power level of the electrical energy in the input signal ultimately determines an applied amplitude (for example, power, current, or voltage) of the one or more electrical pulses created using the electrical energy contained in the input signal. In some implementations, the input signal can contain information based on which stimulus waveforms to be synthesized and applied at the electrodes of the implanted wireless stimulator device 114. In one example, the input signal can encode, for example, delay information, or repetition rate information and waveform characteristics as well address information point to a portion of a read-only memory (ROM) on the implantable stimulator device. In this example, the delay information may indicate the amount of latency that the stimulation waveform may be synthesized. Due to the nature of the PDM encoded waveform, an analog waveform can be represented by a stream of single-bit logic values, instead of multi-bit digital code. The address information refers to the storage location on the ROM to retrieve a pulse-density modulated representation of the desired stimulation waveform.

The RF pulse generator module 106 can be implanted subcutaneously, or it can be worn external to the body. When external to the body, the RF generator module 106 can be incorporated into a belt or harness design to allow for electric radiative coupling through the skin and underlying tissue to transfer power and/or control parameters to the implanted wireless stimulator device 114. In either event, receiver circuit(s) internal to the wireless stimulator device 114 can capture the energy radiated by the TX antenna 110 and use this energy to synthesize a stimulation waveform. The receiver circuit(s) may further modify the waveform to create an electrical pulse suitable for the stimulation of neural tissue.

In some implementations, the RF pulse generator module 106 can remotely control the stimulus parameters (that is, the parameters of the electrical pulses applied to the neural tissue) and monitor feedback from the wireless stimulator device 114 based on RF signals received from the implanted wireless stimulator device 114. A feedback detection algorithm implemented by the RF pulse generator module 106 can monitor data sent wirelessly from the implanted wireless stimulator device 114, including information about the energy that the implanted wireless stimulator device 114 is receiving from the RF pulse generator and information about the tissue characteristics the electrode pads see. In order to provide an effective therapy for a given medical condition, the system can be tuned to provide the optimal amount of excitation or inhibition to the nerve fibers by electrical stimulation. A closed loop feedback control method can be used in which the output signals from the implanted wireless stimulator device 114 are monitored and used to determine the appropriate level of neural stimulation current for maintaining effective neuronal activation, or, in some cases, the patient can manually adjust the output signals in an open loop control method.

Figure 2:
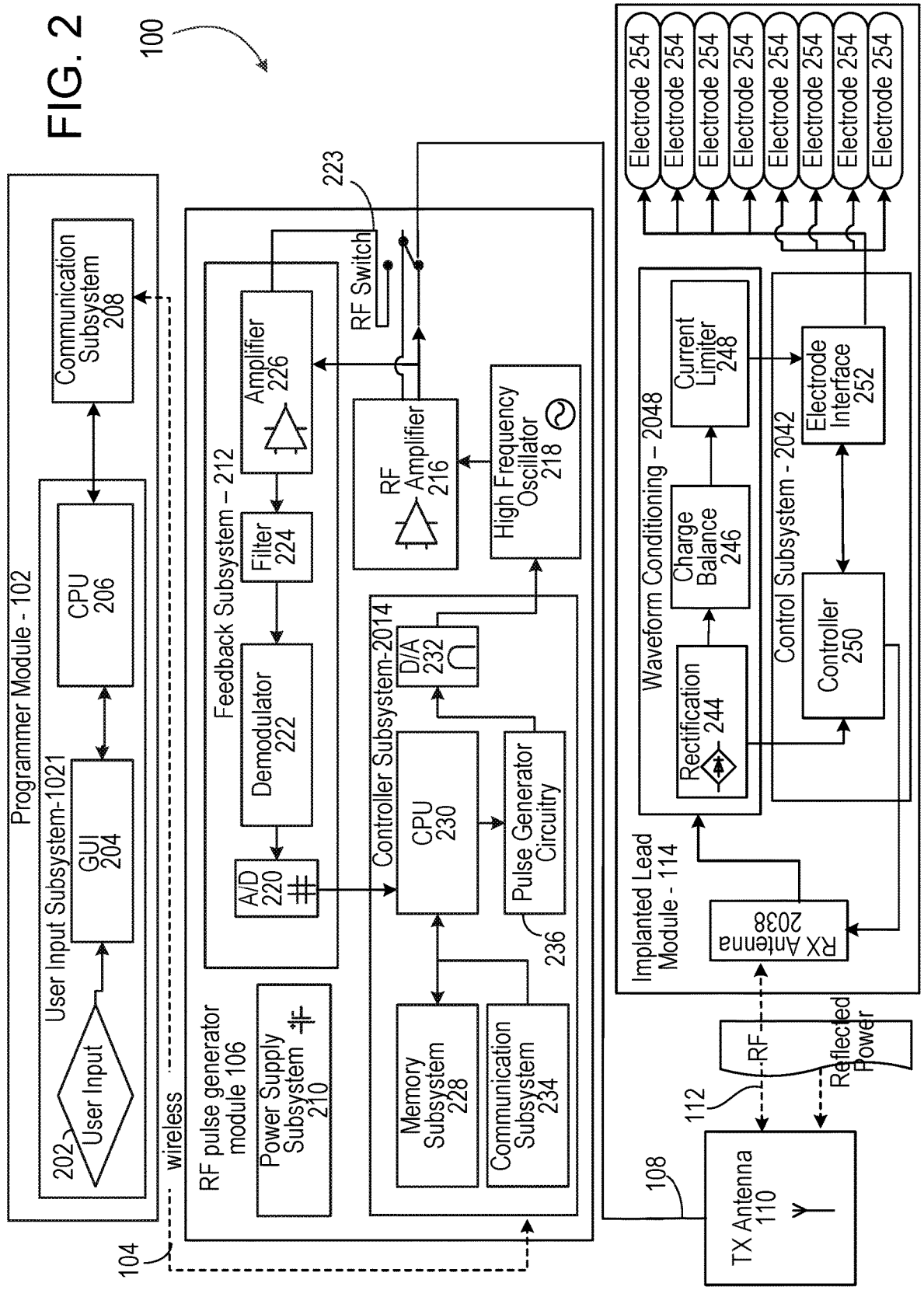
FIG. 2 depicts a detailed diagram of an example of the wireless stimulation system.

FIG. 2 depicts a detailed diagram of an example of the wireless stimulation system. As depicted, the programming module 102 may comprise user input system 202 and communication subsystem 208. The user input system 221 may allow various parameter settings to be adjusted (in some cases, in an open loop fashion) by the user in the form of instruction sets. The communication subsystem 208 may transmit these instruction sets (and other information) via the wireless connection 104, such as Bluetooth or Wi-Fi, to the RF pulse generator module 106, as well as receive data from module 106.

For instance, the programmer module 102, which can be utilized for multiple users, such as a patient's control unit or clinician's programmer unit, can be used to send information to the RF pulse generator module 106 such that stimulation parameters (e.g., pulse amplitude, pulse frequency, and pulse width) can be controlled. Example ranges of stimulation parameters are shown in Table 1. In this context the term pulse refers to the phase of the waveform that directly produces stimulation of the tissue; the parameters of the charge-balancing phase (described below) can similarly be controlled. The patient and/or the clinician can also optionally control overall duration and pattern of treatment.

TABLE 1

| Stimulation Parameter | |
| --- | --- |
| Pulse Amplitude: | 0 to 20 mA |
| Pulse Frequency: | 0 to 10000 Hz |
| Pulse Width: | 0 to 2 ms |

The RF pulse generator module 106 may be initially programmed to meet the specific parameter settings for each individual patient during the initial implantation procedure. Because medical conditions or the body itself can change over time, the ability to re-adjust the parameter settings may be beneficial to ensure ongoing efficacy of the neural modulation therapy.

The programmer module 102 may be functionally a smart device and/or an associated application. The smart device hardware may include a CPU 206 and be used as a vehicle to handle touchscreen input on a graphical user interface (GUI) 204, for processing and storing data.

The RF pulse generator module 106 may be connected via wired connection 108 to an external TX antenna 110. Alternatively, both the antenna and the RF pulse generator are located subcutaneously (not shown).

The signals sent by RF pulse generator module 106 to the implanted wireless stimulator device 114 may include electrical power and configuration data based on which to recover pulse attributes such as stimulus waveform, amplitude, pulse width, and repetition frequency. The configuration data may also include polarity setting information designating the polarity setting for each electrode. The RF pulse generator module 106 can also function as a wireless receiving unit that receives feedback signals from the implanted wireless stimulator device 114. To that end, the RF pulse generator module 106 may contain microelectronics or other circuitry to handle the generation of the signals transmitted to the device 114 as well as handle feedback signals, such as those from the stimulator device 114. For example, the RF pulse generator module 106 may comprise controller subsystem 214, high-frequency oscillator 218, RF amplifier 216, a RF switch, and a feedback subsystem 212.

The controller subsystem 214 may include a CPU 230 to handle data processing, a memory subsystem 228 such as a local memory, communication subsystem 234 to communicate with programmer module 102 (including receiving stimulation parameters from programmer module), pulse generator circuitry 236, and single-bit oversampled (ΣΔ) digital/analog (D/A) converters or single-bit controlled full-bridge drivers 232. In other implementations, a Nyquist rate multi-bit D/A converters can also be used for stimulus generation.

The controller subsystem 214 may be used by the patient and/or the clinician to control the stimulation parameter settings (for example, by controlling the parameters of the signal sent from RF pulse generator module 106 to the stimulator device 114). These parameter settings can affect, for example, the power, current level, or shape of the one or more electrical pulses. The programming of the stimulation parameters can be performed using the programming module 102, as described above, to set the repetition rate, pulse width, amplitude, and waveform that will be transmitted by RF energy to the receiving (RX) antenna 238, typically a dipole antenna (although other types may be used), in the implanted wireless stimulation device 214. The clinician may have the option of locking and/or hiding certain settings within the programmer interface, thus limiting the patient's ability to view or adjust certain parameters because adjustment of certain parameters may require detailed medical knowledge of neurophysiology, neuroanatomy, protocols for neural modulation, and safety limits of electrical stimulation.

The controller subsystem 214 may store received parameter settings in the local memory subsystem 228, until the parameter settings are modified by new input data received from the programming module 102. The CPU 206 may use the parameters stored in the local memory to control the pulse generator circuitry 236 to generate a signal that would enable the synthesis of the desired stimulation waveform on the implantable stimulator device 114. The signal can be modulated by a high frequency carrier signal generated by an oscillator 218 in the range from 300 MHz to 8 GHz (preferably between about 700 MHz and 5.8 GHz and more preferably between about 800 MHz and 1.3 GHz). The resulting RF signal may then be amplified by RF amplifier 226 and then sent through an RF switch 223 to the TX antenna 110 to reach through depths of tissue to the RX antenna 238. In the case where a single-bit pulse density modulated waveform is used for stimulus generation, a local oscillator in the range of 1 MHz is used to read-in the bitstream from a ROM device.

In some implementations, the RF signal sent by TX antenna 110 may simply be a power transmission signal used by the wireless stimulation device module 114 to generate electric pulses. In other implementations, a telemetry signal may also be transmitted to the wireless stimulator device 114, which telemetry signal includes instructions about the various operations of the wireless stimulator device 114. The telemetry signal may be sent by the modulation of the carrier signal (through the skin if external, or through other body tissues if the pulse generator module 106 is implanted subcutaneously). The telemetry signal is used to modulate the carrier signal (a high frequency signal) using one of the several modulation methods including On-Off Keying (OOK), Pulse-Amplitude Modulation (PAM), Phase-shift Keying (PSK) and Frequency-Shift Keying (FSK) and does not interfere with the input received on the same stimulator device to power the device. In one embodiment the telemetry signal and powering signal are combined into one signal, where the RF telemetry signal is used to modulate the RF powering signal, and thus the wireless stimulation device is powered directly by the received telemetry signal; separate subsystems in the wireless stimulation device harness the power contained in the signal and interpret the data content of the signal.

The RF switch 223 may be a multipurpose device such as a dual directional coupler, which passes the relatively high amplitude, extremely short duration RF pulse to the TX antenna 110 with minimal insertion loss while simultaneously providing two low-level outputs to feedback subsystem 212; one output delivers a forward power signal to the feedback subsystem 212, where the forward power signal is an attenuated version of the RF pulse sent to the TX antenna 110, and the other output delivers a reverse power signal to a different port of the feedback subsystem 212, where reverse power is an attenuated version of the reflected RF energy from the TX Antenna 110.

During the on-cycle time (when an RF signal is being transmitted to wireless stimulator device 114), the RF switch 223 is set to send the forward power signal to feedback subsystem. During the off-cycle time (when an RF signal is not being transmitted to the wireless stimulator device 114), the RF switch 223 can change to a receiving mode in which the reflected RF energy and/or RF signals from the wireless stimulator device 114 are received to be analyzed in the feedback subsystem 212.

The feedback subsystem 212 of the RF pulse generator module 106 may include reception circuitry to receive and extract telemetry or other feedback signals from the wireless stimulator device 114 and/or reflected RF energy from the signal sent by TX antenna 110. The feedback subsystem may include an amplifier 226, a filter 224, a demodulator 222, and an A/D converter 220.

The feedback subsystem 212 receives the forward power signal and converts this high-frequency AC signal to a DC level that can be sampled and sent to the controller subsystem 214. In this way the characteristics of the generated RF pulse can be compared to a reference signal within the controller subsystem 214. If a disparity (error) exists in any parameter, the controller subsystem 214 can adjust the output to the RF pulse generator 106. The nature of the adjustment can be, for example, proportional to the computed error. The controller subsystem 214 can incorporate additional inputs and limits on its adjustment arrangements such as the signal amplitude of the reverse power and any predetermined maximum or minimum values for various pulse parameters.

The reverse power signal can be used to detect fault conditions in the RF-power delivery system. In an ideal condition, when TX antenna 110 has perfectly matched impedance to the tissue that it contacts, the electromagnetic waves generated from the RF pulse generator 106 pass unimpeded from the TX antenna 110 into the body tissue. However, in real-world applications a large degree of variability may exist in the body types of users, types of clothing worn, and positioning of the antenna 110 relative to the body surface. Since the impedance of the antenna 110 depends on the relative permittivity of the underlying tissue and any intervening materials, and also depends on the overall separation distance of the antenna from the skin, in any given application there can be an impedance mismatch at the interface of the TX antenna 110 with the body surface. When such a mismatch occurs, the electromagnetic waves sent from the RF pulse generator 106 are partially reflected at this interface, and this reflected energy propagates backward through the antenna feed.

The dual directional coupler RF switch 223 may prevent the reflected RF energy propagating back into the amplifier 226, and may attenuate this reflected RF signal and send the attenuated signal as the reverse power signal to the feedback subsystem 212. The feedback subsystem 212 can convert this high-frequency AC signal to a DC level that can be sampled and sent to the controller subsystem 214. The controller subsystem 214 can then calculate the ratio of the amplitude of the reverse power signal to the amplitude of the forward power signal. The ratio of the amplitude of reverse power signal to the amplitude level of forward power may indicate severity of the impedance mismatch.

In order to sense impedance mismatch conditions, the controller subsystem 214 can measure the reflected-power ratio in real time, and according to preset thresholds for this measurement, the controller subsystem 214 can modify the level of RF power generated by the RF pulse generator 106. For example, for a moderate degree of reflected power the course of action can be for the controller subsystem 214 to increase the amplitude of RF power sent to the TX antenna 110, as would be needed to compensate for slightly non-optimum but acceptable TX antenna coupling to the body. For higher ratios of reflected power, the course of action can be to prevent operation of the RF pulse generator 106 and set a fault code to indicate that the TX antenna 110 has little or no coupling with the body. This type of reflected-power fault condition can also be generated by a poor or broken connection to the TX antenna. In either case, it may be desirable to stop RF transmission when the reflected-power ratio is above a defined threshold, because internally reflected power can lead to unwanted heating of internal components, and this fault condition means the system cannot deliver sufficient power to the implanted wireless stimulation device and thus cannot deliver therapy to the user.

The controller 242 of the wireless stimulator device 114 may transmit informational signals, such as a telemetry signal, through the antenna 238 to communicate with the RF pulse generator module 106 during its receive cycle. For example, the telemetry signal may be coupled to the modulated signal on the dipole antenna(s) 238, during the on and off state of the transistor circuit to enable or disable a waveform that produces the corresponding RF bursts necessary to transmit to the external (or remotely implanted) pulse generator module 106. The antenna(s) 238 may be connected to electrodes 254 in contact with tissue to provide a return path. An A/D (not shown) converter can be used to transform stored data to a serialized pattern that can be transmitted on the pulse-modulated telemetry signal from the internal antenna(s) 238 of the wireless stimulator device 114.

A telemetry signal from the implanted wireless stimulator device 114 may include stimulus parameters such as the power or the amplitude of the current that is delivered to the tissue from the electrodes, or impedance of the tissue. The feedback signal can be transmitted to the RF pulse generator module 116 to indicate the strength of the stimulus at the nerve bundle by means of coupling the signal to the implanted RX antenna 238, which radiates the telemetry signal to the external (or remotely implanted) RF pulse generator module 106. The feedback signal can include either or both an analog and digital telemetry pulse modulated carrier signal. Data such as stimulation pulse parameters and measured characteristics of stimulator performance can be stored in an internal memory device within the implanted stimulator device 114, and sent on the telemetry signal. The frequency of the carrier signal may be in the range of at 300 MHz to 8 GHz (preferably between about 700 MHz and 5.8 GHz and more preferably between about 800 MHz and 1.3 GHz).

In the feedback subsystem 212, the telemetry signal can be down modulated using demodulator 222 and digitized by being processed through an analog to digital (A/D) converter 220. The digital telemetry signal may then be routed to a CPU 230 with embedded code, with the option to reprogram, to translate the signal into a corresponding current measurement in the tissue based on the amplitude of the received signal. The CPU 230 of the controller subsystem 214 can compare the reported stimulus parameters to those held in local memory 228 to verify the wireless stimulator device 114 delivered the specified stimuli to tissue. For example, if the wireless stimulation device reports a lower current than was specified, the power level from the RF pulse generator module 106 can be increased so that the implanted wireless stimulator device 114 will have more available power for stimulation. The implanted wireless stimulator device 114 can generate telemetry data in real time, for example, at a rate of 8 Kbits per second. All feedback data received from the implanted stimulator device 114 can be logged against time and sampled to be stored for retrieval to a remote monitoring system accessible by the health care professional for trending and statistical correlations.

The sequence of remotely programmable RF signals received by the internal antenna(s) 238 may be conditioned into waveforms that are controlled within the implantable wireless stimulator device 114 by the control subsystem 242 and routed to the appropriate electrodes 254 that are placed in proximity to the tissue to be stimulated. For instance, the RF signal transmitted from the RF pulse generator module 106 may be received by RX antenna 238 and processed by circuitry, such as waveform generation circuitry 240, within the implanted wireless stimulator device 114 to be converted into electrical pulses applied to the electrodes 254 through electrode interface 252. In some implementations, the implanted wireless stimulator device 114 contains between two to sixteen electrodes 254.

The waveform conditioning and generation circuitry 240 may include a rectifier 244, which rectifies the signal received by the RX antenna 238. The rectified signal may be fed to the controller 242 for receiving encoded instructions from the RF pulse generator module 106. The rectifier signal may also be fed to a charge balance component 246 that is configured to create one or more electrical pulses based such that the one or more electrical pulses result in a substantially zero net charge at the one or more electrodes (that is, the pulses are charge balanced with zero net charge output). The charge-balanced pulses are passed through the current limiter 248 to the electrode interface 252, which applies the pulses to the electrodes 254 as appropriate.

The current limiter 248 insures the current level of the pulses applied to the electrodes 254 is not above a threshold current level. In some implementations, an amplitude (for example, current level, voltage level, or power level) of the received RF pulse (i.e., the input signal) directly determines the amplitude of the stimulus. In this case, it may be particularly beneficial to include current limiter 248 to prevent excessive current or charge being delivered through the electrodes, although current limiter 248 may be used in other implementations where this is not the case. Generally, for a given electrode having several square millimeters surface area, it is the charge per phase that should be limited for safety (where the charge delivered by a stimulus phase is the integral of the current). But, in some cases, the limit can instead be placed on the current, where the maximum current multiplied by the maximum possible pulse duration is less than or equal to the maximum safe charge. More generally, the limiter 248 acts as a charge limiter that limits a characteristic (for example, current or duration) of the electrical pulses so that the charge per phase remains below a threshold level (typically, a safe-charge limit).

In the event the implanted wireless stimulator device 114 receives a "strong" pulse of RF power sufficient to generate a stimulus that would exceed the predetermined safe-charge limit, the current limiter 248 can automatically limit or "clip" the stimulus phase to maintain the total charge of the phase within the safety limit. The current limiter 248 may be a passive current limiting component that cuts the signal to the electrodes 254 once the safe current limit (the threshold current level) is reached. Alternatively, or additionally, the current limiter 248 may communicate with the electrode interface 252 to turn off all electrodes 254 to prevent tissue damaging current levels.

A clipping event may trigger a current limiter feedback control mode. The action of clipping may cause the controller to send a threshold power data signal to the pulse generator 106. The feedback subsystem 212 detects the threshold power signal and demodulates the signal into data that is communicated to the controller subsystem 214. The controller subsystem 214 algorithms may act on this current-limiting condition by specifically reducing the RF power generated by the RF pulse generator, or cutting the power completely. In this way, the pulse generator 106 can reduce the RF power delivered to the body if the implanted wireless stimulator device 114 reports it is receiving excess RF power.

The controller 250 of the stimulator 205 may communicate with the electrode interface 252 to control various aspects of the electrode setup and pulses applied to the electrodes 254. The electrode interface 252 may act as a multiplex and control the polarity and switching of each of the electrodes 254. For instance, in some implementations, the wireless stimulator 106 has multiple electrodes 254 in contact with tissue, and for a given stimulus the RF pulse generator module 106 can arbitrarily assign one or more electrodes to 1) act as a stimulating electrode, 2) act as a return electrode, or 3) be inactive by communication of assignment sent wirelessly with the parameter instructions, which the controller 250 uses to set electrode interface 252 as appropriate. It may be physiologically advantageous to assign, for example, one or two electrodes as stimulating electrodes and to assign all remaining electrodes as return electrodes.

Also, in some implementations, for a given stimulus pulse, the controller 250 may control the electrode interface 252 to divide the current arbitrarily (or according to instructions from pulse generator module 106) among the designated stimulating electrodes. This control over electrode assignment and current control can be advantageous because in practice the electrodes 254 may be spatially distributed along various neural structures, and through strategic selection of the stimulating electrode location and the proportion of current specified for each location, the aggregate current distribution in tissue can be modified to selectively activate specific neural targets. This strategy of current steering can improve the therapeutic effect for the patient.

In another implementation, the time course of stimuli may be arbitrarily manipulated. A given stimulus waveform may be initiated at a time T_start and terminated at a time T_final, and this time course may be synchronized across all stimulating and return electrodes; further, the frequency of repetition of this stimulus cycle may be synchronous for all the electrodes. However, controller 250, on its own or in response to instructions from pulse generator 106, can control electrode interface 252 to designate one or more subsets of electrodes to deliver stimulus waveforms with non-synchronous start and stop times, and the frequency of repetition of each stimulus cycle can be arbitrarily and independently specified.

For example, a stimulator having eight electrodes may be configured to have a subset of five electrodes, called set A, and a subset of three electrodes, called set B. Set A might be configured to use two of its electrodes as stimulating electrodes, with the remainder being return electrodes. Set B might be configured to have just one stimulating electrode. The controller 250 could then specify that set A deliver a stimulus phase with 3 mA current for a duration of 200 us followed by a 400 us charge-balancing phase. This stimulus cycle could be specified to repeat at a rate of 60 cycles per second. Then, for set B, the controller 250 could specify a stimulus phase with 1 mA current for duration of 500 us followed by a 800 us charge-balancing phase. The repetition rate for the set-B stimulus cycle can be set independently of set A, say for example it could be specified at 25 cycles per second. Or, if the controller 250 was configured to match the repetition rate for set B to that of set A, for such a case the controller 250 can specify the relative start times of the stimulus cycles to be coincident in time or to be arbitrarily offset from one another by some delay interval.

Figure 6A:
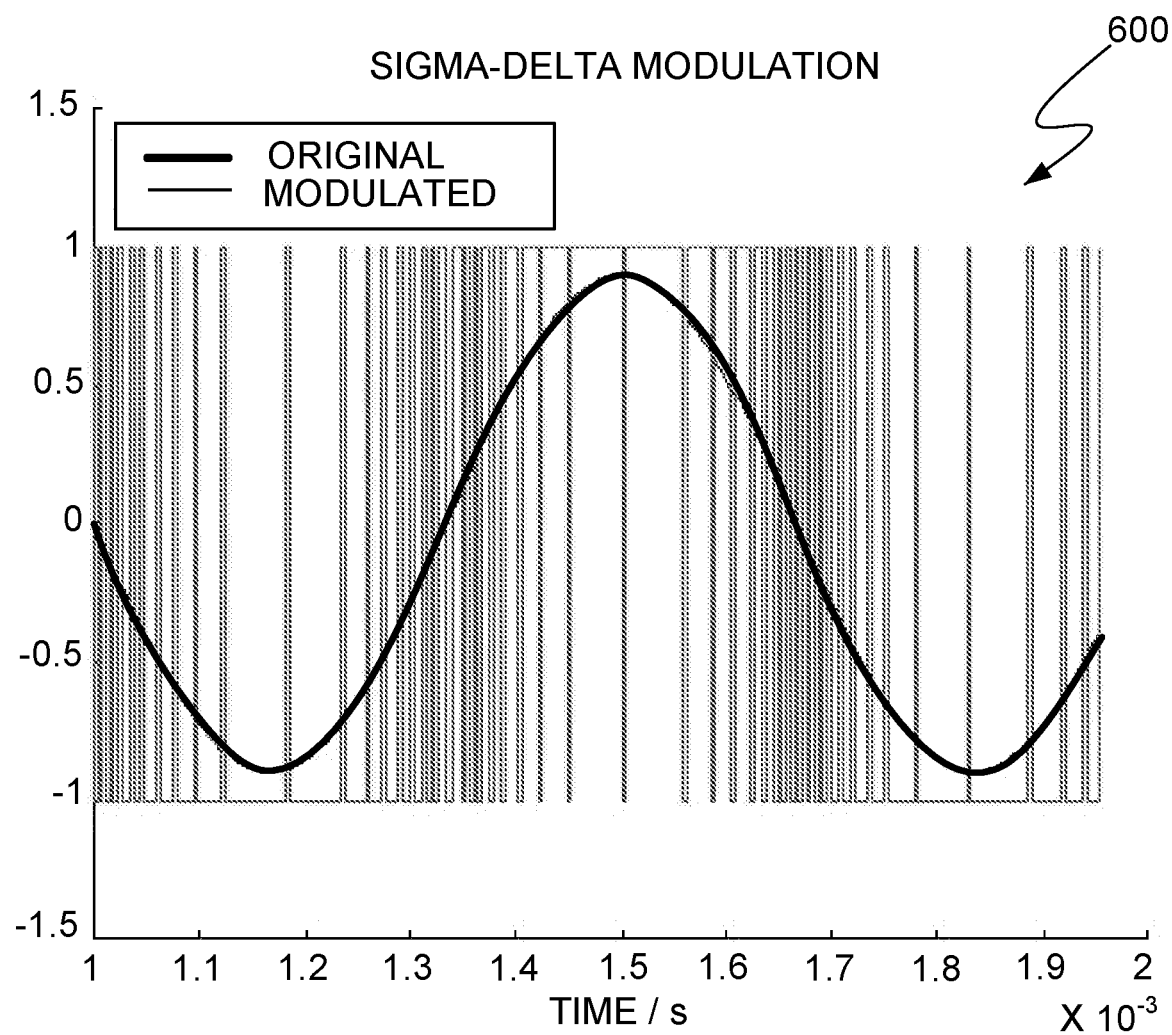
FIGS. 6A-6B show examples of waveforms synthesized using pulse-density modulation.

In some implementations, the controller 250 can include a Read-Only Memory (ROM) device that stores pulse-density modulated signals with varying pulse parameters. Referring to FIGS. 6A-6B, 7-12, pulse-density modulation (PDM) signals can be used by implantable stimulator device 114 to synthesize an desirable stimulation waveform applied at an electrode. Although the stored signal can be a single-bit representation of the amplitude information of the stimulation waveform, when the stored signal is read-in and played by a single-bit D/A converter or a driver, a stimulation waveform can be synthesized at the electrodes, for example, by an integrate-and-hold component on the implantable stimulator device. The single-bit PDM encoded stimulus waveform is computed using a digital ΣΔ noise shaper offline and stored into the on-chip ASIC. In more detail, FIG. 6A shows an example of pulse-density modulation of a sinusoid waveform. As illustrated, the density of '1's and '−1's define the amplitude of the sinusoidal waveform. In other words, during temporal periods of more rapid changes in amplitude, the amplitude may see higher density of encoding. In particular, a "1" may represent an increment in amplitude over the previously encoded waveform amplitude. Meanwhile, a "−1" may represent a decrement in amplitude over the previously encoded waveform amplitude. In general, the stored signal is sampled at rates 40 to 60 times or more as high as the pitch frequency of the sinusoid waveform, which is called oversampling. The higher the oversampling rate, the lower the quantization artifacts, and noise associated with waveform quantization gets. The oversampling can be leveraged in synthesizing the analog form of the stimulation waveform, which can have an arbitrary shape suitable for stimulation neural tissue. The synthesis may include a demodulation process using the integrate-and-hold component. Due to purely digital nature of the PDM waveform, the DC offset associated with the encoded signal can be pushed down to zero by simply monitoring the DC content at the output and fine tuning the on-off durations of +1 and −1 periods. This ensures that the stimulus waveform is already digitally charge-balanced without the need for external DC blocking.

Figure 6B:
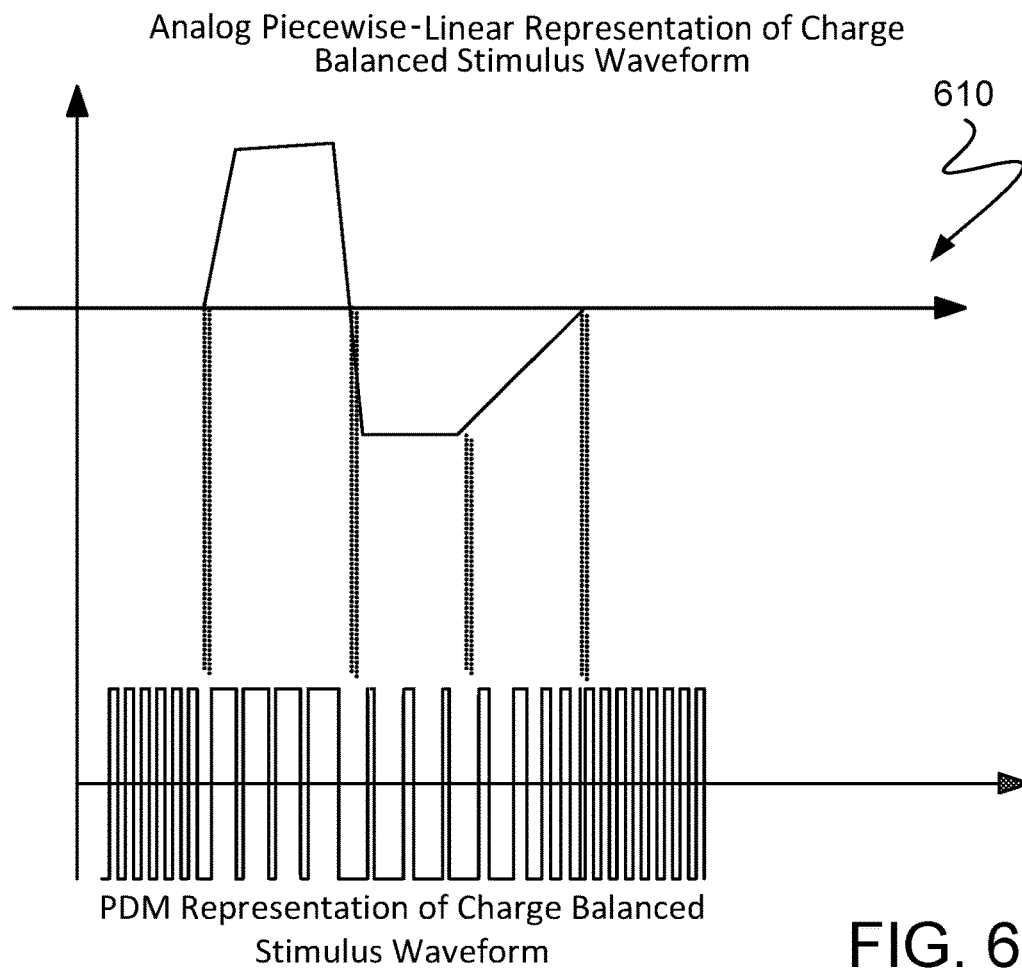

Applying the PDM encoding can synthesize charge-balanced neurostimulation waveforms, as illustrated in FIG. 6B. The top panel shows a desired neurostimulation waveform. In particular, the desired neurostimulation waveform is suitable for application at an electrode. Moreover, this stimulation waveform has a particular shape that is charge balanced so that the net charge released by the electrode is zero. In one implementation, an instance of the desired neurostimulation waveform, as represented by the PDM encoding approach and illustrated in the bottom panel of FIG. 6B, is stored in a ROM device on implantable stimulator device 114. In this implementation, the ROM device can be located on controller 250. The stored instance of the desired neurostimulation waveform can be retrieved from the ROM and then played, for example, through a low-pass network that includes the integrate-and-hold component and functions as a demodulator. In particular the single-bit PDM encoding already contains, in the low-frequency spectrum, the desired stimulus signal. Indeed, FIG. 8 illustrates spectral components 804A, 804B, and 804C from the spectrum of a single-bit PDM encoded signal. As illustrated, spectral component 804A is within the low frequency region 802. Indeed, a desired stimulation waveform can be synthesized based on spectral component 804A. In some implementations, the low-pass spectral characteristic of analog circuits driving the electrodes as well as the capacitive nature of tissue impedance can function as an analog integrative reconstruction filter such that a desired waveform of arbitrary shape is created consistently in a repeatable manner and irrespective of the spectral characteristic within low-pass region 802. When the instance of the stored waveform is being played, the stored instance may be serially shifted outward to match a preferred pulse duration. The amplitude of the synthesized stimulation waveform at electrodes 254 may ultimately depend on the power supply level and is subject to the current limiting/clipping restrictions discussed herein. In these implementations, the synthesis solely uses electrical energy contained in the input signal transmitted from pulse generator 106 and received by the implantable neural stimulator device 114.

Figure 7:
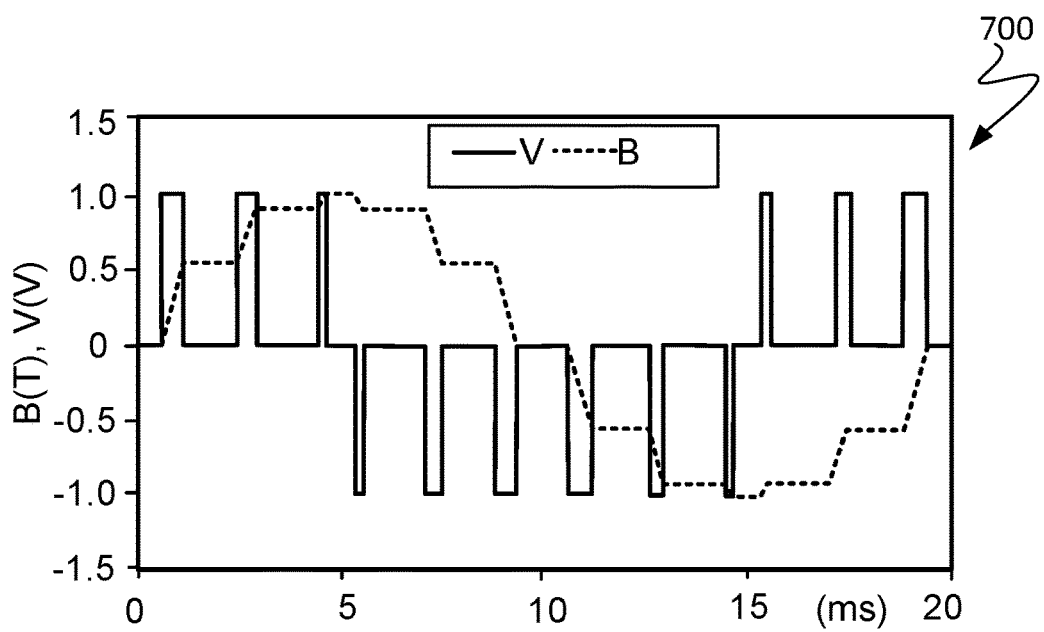
FIG. 7 shows an example of a charge balanced waveform synthesized using pulse-density modulation.

FIG. 7 illustrates another example of a charged-balanced stimulation waveform of one cycle, as synthesized by implantable stimulator device 114. The PDM encoded single-bit format may be stored on the implantable stimulator device and retrieved according to an instruction in the input signal transmitted from pulse generator 106. In some implementations, multiple stimulation waveforms, with different and arbitrary shapes for particular stimulation contexts, can be stored on a ROM device on the implantable neural stimulator device 114. The stored instances can be encoded in PDM format such that when a stored instance is retrieved from the ROM device, a demodulation can reconstruct the desired stimulation waveform from this instance. Moreover, the input signal may contain information to select a particular instance in the PDM format so that a desired stimulation waveform can be reconstructed and synthesized.

Thus, some implementations may reconstruct stimulation waveforms of arbitrary shape at the electrodes. In these implementations, the reconstructed waveform may be in response to instructions from pulse generator 106. The stimulus phase may be delivered by a constant-current source or a constant-voltage source, and this type of control may generate characteristic waveforms that are static, e.g. a constant-current source generates a characteristic rectangular pulse in which the current waveform has a very steep rise, a constant amplitude for the duration of the stimulus, and then a very steep return to baseline. Alternatively, or additionally, the controller 250 can increase or decrease the level of current at any time during the stimulus phase and/or during the charge-balancing phase. Thus, in some implementations, the controller 250 can deliver arbitrarily shaped stimulus waveforms such as a triangular pulse, sinusoidal pulse, or Gaussian pulse for example. Similarly, the charge-balancing phase can be arbitrarily amplitude-shaped, and similarly a leading anodic pulse (prior to the stimulus phase) may also be amplitude-shaped.

Figure 9A:
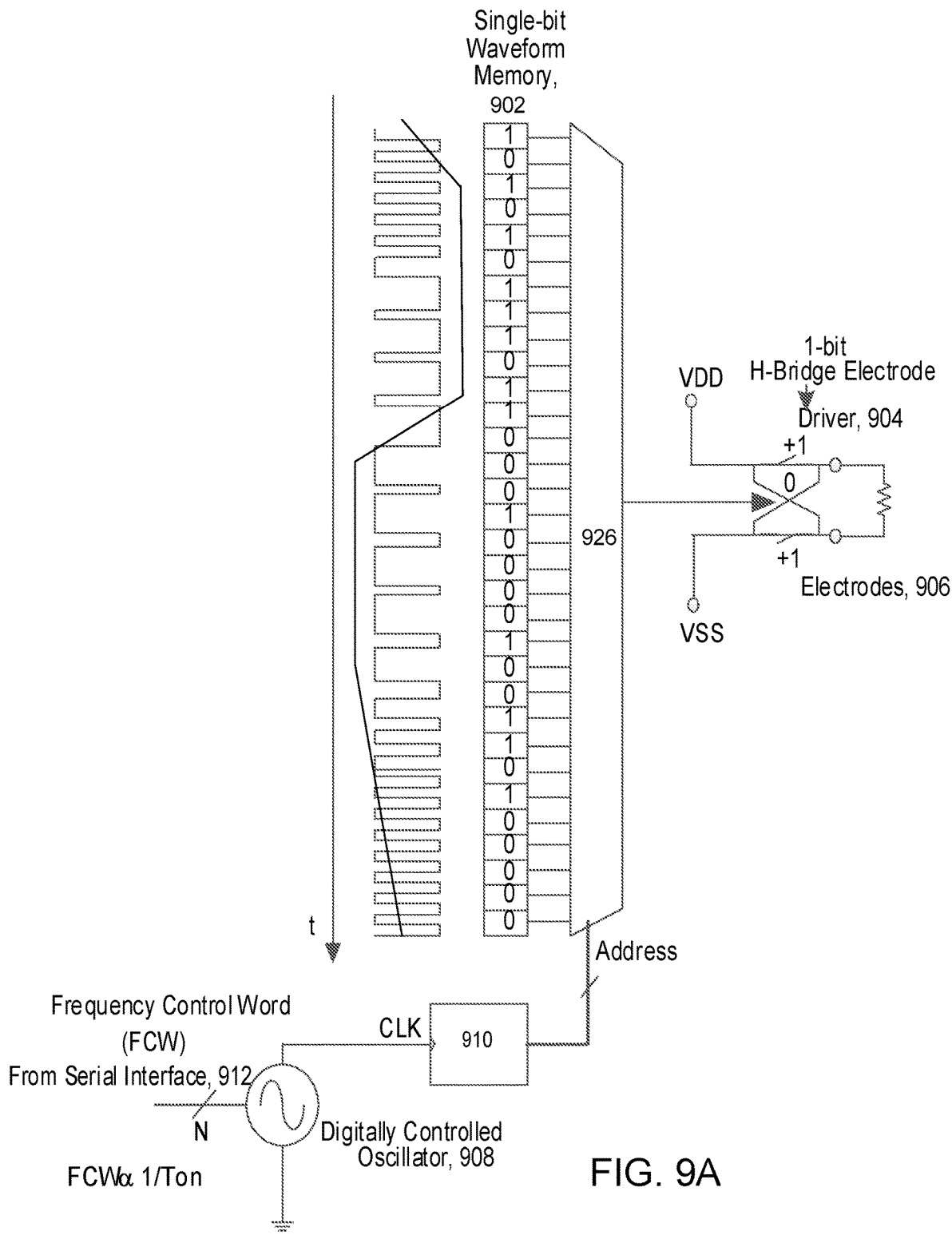
FIGS. 9A-9B shows examples of single-bit waveform memory coupled to electrode driver.
Figure 9B:
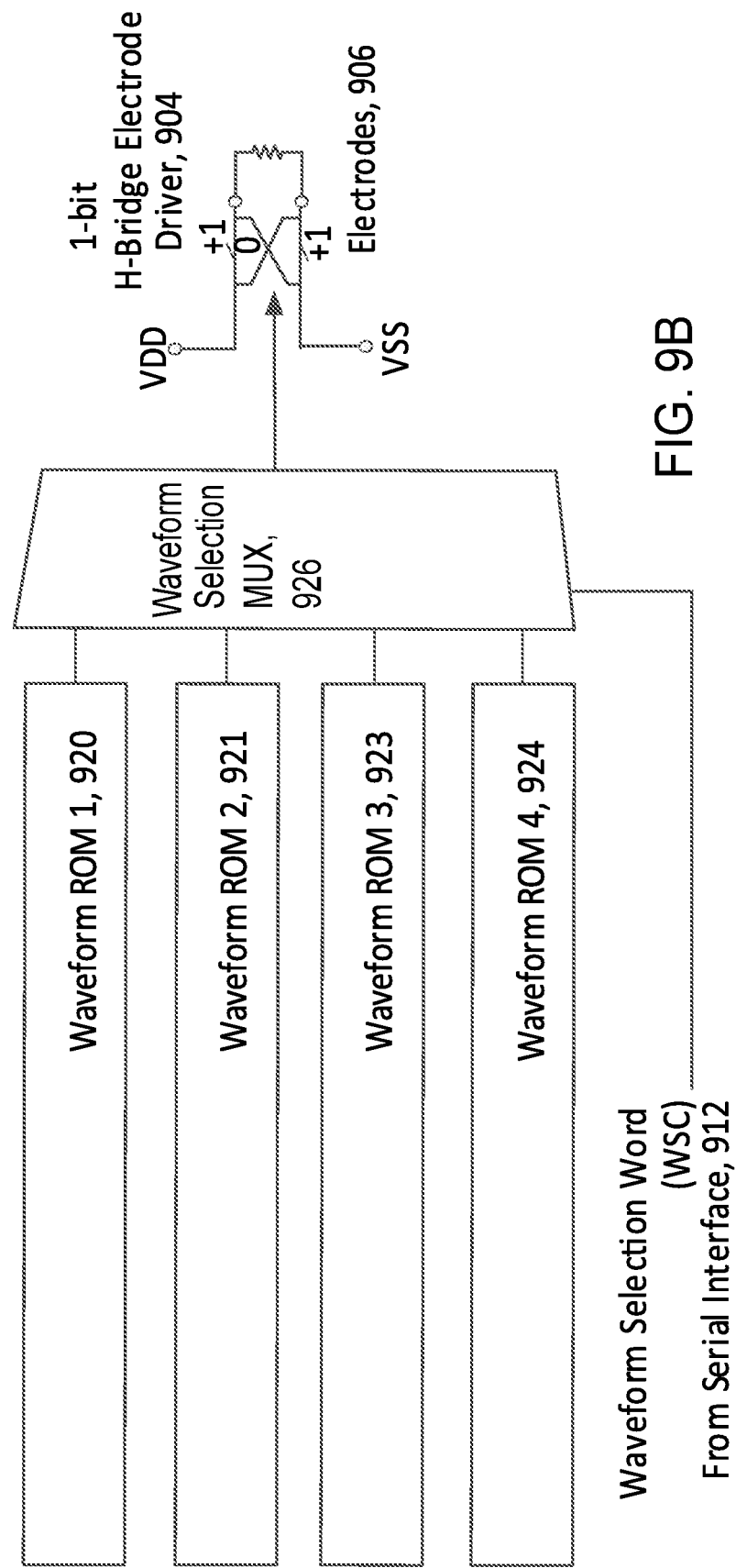

A charge balanced bi-phase stimulus waveform can be converted to a pulse density modulated Bitstream. Some implementations may use a digital oversampling ΣΔ modulator to effectively map the analog charge balanced stimulus waveform. In these implementations, single bit bitstream that represents the waveform can be stored a priori in ASIC ROM. For example, the single bit waveform memory 902 can be loaded with information that has been calculated off-line, and based on pulse parameters such as the pulse duration information—as transmitted from the microwave field stimulator (MFS), the stimulation waveform can be synthesized when the clocking speed of the serial interface (e.g., clock 910 on serial interface 912 that controls oscillator 908) determines the pulse duration of the synthesized waveform. Referring particularly to FIGS. 9A and 9B, the synthesized waveform is provided to 1-bit H-bridge (i.e., full bridge) electrode driver 904, which couples to electrode 906. FIG. 9B particular illustrates that waveform ROM 920 to 924 are coupled to MUX 926 such that one is selected per waveform selection word (WSC) from serial interface 912.

Figure 10A:
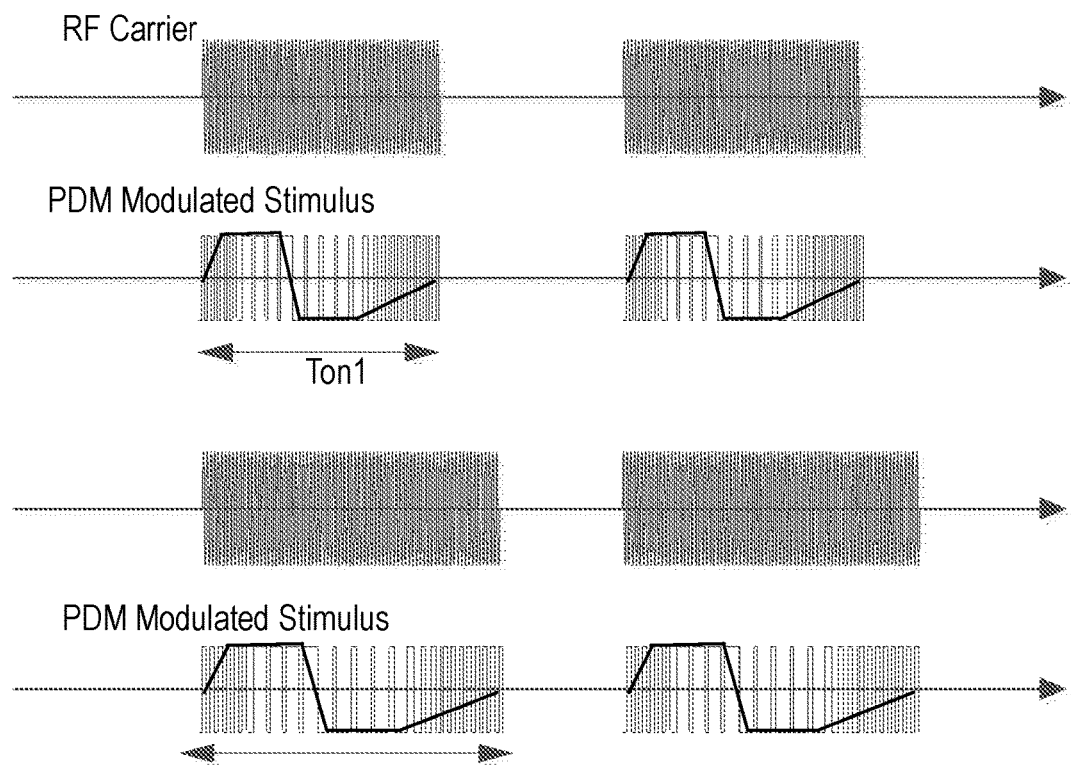
FIGS. 10A-10B shows examples of adjusting duration and amplitude of PDM waveforms.
Figure 10B:
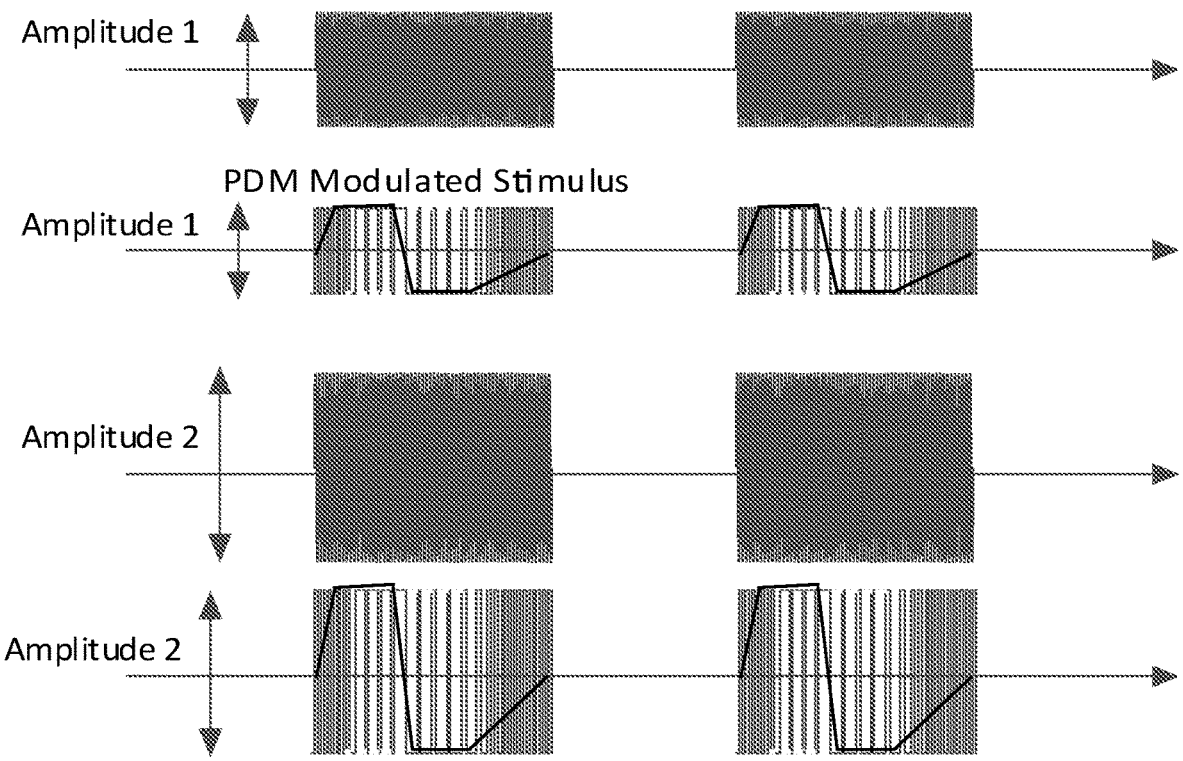

FIG. 10A illustrates that the duration of the stimulus pulse can be modulated by extending serializer clock period (slowing down the serializer clock frequency). In particular, the read-out clock that is used for playing the PDM waveform is generated by a digitally controlled oscillator 908. For longer duration waveforms, the clock is slowed down—for example, leading to PDM modulated stimulus ton2, and for shorter duration pulses, the clock is sped up—for example, leading to PDM modulated stimulus ton1. This can preserve a fixed oversampling ratio for the PDM waveform. The amplitude of the waveform is controlled by the DC level of the full bridge driver that affects amplitude of PDM modulated stimulus, as illustrated in FIG. 10B.

Figure 11:
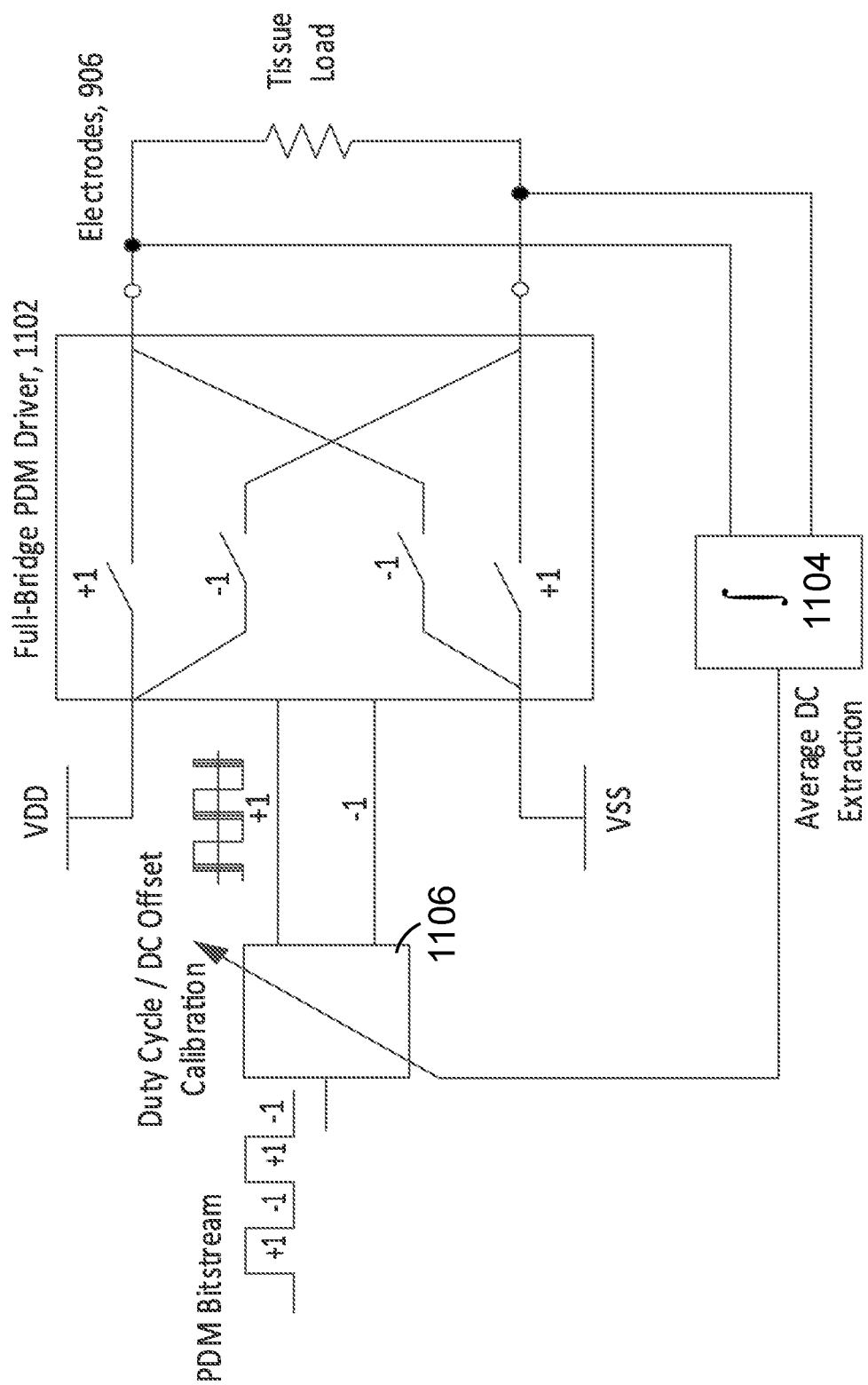
FIG. 11 shows an example of a full-bridge PDM driver.
Figure 12:
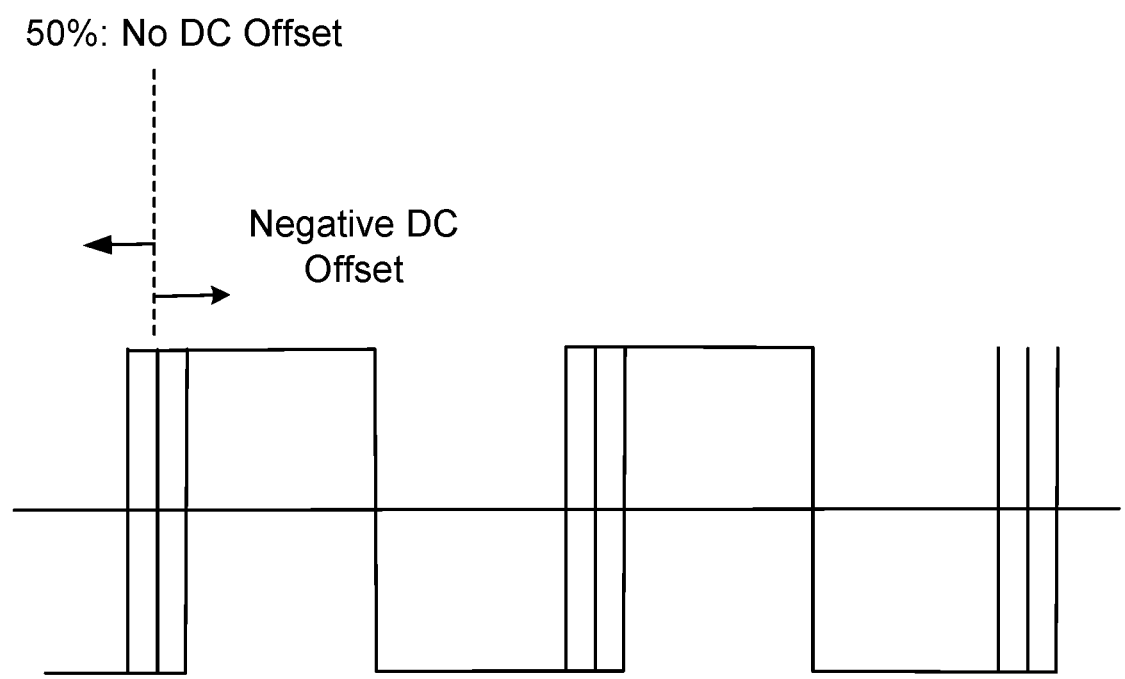
FIG. 12 shows an example of adjusting pulse-width to fine tune DC offset.

DC blocking capacitors can be to drive the stimulator's electrodes to avoid positive or negative charge accumulating in the tissue. Due to low-frequency nature of the stimulus waveform, and low tissue resistance, the capacitance value can be in in the range of tens of uFarads. In some implementations, and DC servo loop may be used to sense and integrate DC offset across the tissue and provide the information as feedback to correct for the duty cycle of the PDM bitstream. FIG. 11 shows an example of an implementation of duty cycle corrected, DC offset canceling full bridge PDM driver 1102. In this implementation DC servo loop, including average DC extraction 1104 and Duty Cycle/DC Offset calibration 1106, can be used in instrumentation amplifiers to extract average DC level of a signal and cancel from the DC offset from the input signal. In this approach, DC offset is caused by the duty cycle mismatch in the readout clock waveform. This offset may be collected by average DC extraction 1104 and then provided as feedback to duty cycle/DC offset calibration 1106. In this example, the servo loop is used to correct the duty cycle of the input waveform, the PDM bitstream. A perfect 50% duty cycle square wave waveform would have zero information. However due to deviations in the duty cycle net positive or negative DC offset can be accumulated across the tissue. As shown in FIG. 12, by adjusting the on duration based on servo loop back, the DC offset can be fined tuned to be zero.

As described above, the wireless stimulator device 114 may include a charge-balancing component 246. Generally, for constant current stimulation pulses, pulses should be charge balanced by having the amount of cathodic current to be equal the amount of anodic current, which is typically called biphasic stimulation. Charge density is the amount of current times the duration it is applied, and is typically expressed in the units $uC/cm^2$. In order to avoid the irreversible electrochemical reactions such as pH change, electrode dissolution as well as tissue destruction, no net charge should appear at the electrode-electrolyte interface, and it is generally acceptable to have a charge density less than 30 $uC/cm^2$. Biphasic stimulating current pulses ensure that no net charge appears at the electrode after each stimulation cycle and the electrochemical processes are balanced to prevent net dc currents. The wireless stimulator device 114 may be designed to ensure that the resulting stimulus waveform has a net zero charge. Charge balanced stimuli are thought to have minimal damaging effects on tissue by reducing or eliminating electrochemical reaction products created at the electrode-tissue interface.

A stimulus pulse may have a negative-voltage or current, called the cathodic phase of the waveform. Stimulating electrodes may experience both cathodic and anodic phases at different times during the stimulus cycle. An electrode that delivers a negative current with sufficient amplitude to stimulate adjacent neural tissue is called a "stimulating electrode." During the stimulus phase the stimulating electrode acts as a current sink. One or more additional electrodes act as a current source and these electrodes are called "return electrodes." Return electrodes are placed elsewhere in the tissue at some distance from the stimulating electrodes. When a typical negative stimulus phase is delivered to tissue at the stimulating electrode, the return electrode has a positive stimulus phase. During the subsequent charge-balancing phase, the polarities of each electrode are reversed.

In some applications, the charge balance component 246 can include a blocking capacitor(s) placed electrically in series with the stimulating electrodes and body tissue, between the point of stimulus generation within the stimulator circuitry and the point of stimulus delivery to tissue. In these implementations, the tissue impedance and additional filtering capacitance can form an AC band-pass filter that reconstructs the charge balanced waveform. In a multi-electrode stimulator, one charge-balance capacitor(s) may be used for each electrode or a centralized capacitor(s) may be used within the stimulator circuitry prior to the point of electrode selection. The AC high-pass filter can block direct current (DC). However, in some instances, it can also prevent low-frequency alternating current (AC) from passing to the tissue. The frequency below which the series RC network essentially blocks signals is commonly referred to as the cutoff frequency, and in one embodiment the design of the stimulator system may ensure the cutoff frequency is low enough such that the desired stimulus waveform can pass without a significant filtering. In this embodiment as disclosed herein, the wireless stimulator may have a charge-balance capacitor with a value chosen according to the measured series resistance of the electrodes and the tissue environment in which the stimulator is implanted. By selecting a specific capacitance value, the cutoff frequency of the AC high-pass filter in this embodiment can be, for example, at or below the fundamental frequency of the stimulus pulse.

In other implementations, the cutoff frequency may be chosen to be at or above the fundamental frequency of the stimulus, and in this scenario the stimulus waveform created prior to the charge-balance capacitor, called the drive waveform, may be designed to be non-stationary, where the envelope of the drive waveform is varied during the duration of the drive pulse. For example, in one embodiment, the initial amplitude of the drive waveform is set at an initial amplitude Vi, and the amplitude is increased during the duration of the pulse until it reaches a final value k*Vi. By changing the amplitude of the drive waveform over time, the shape of the stimulus waveform passed through the charge-balance capacitor is also modified. The shape of the stimulus waveform may be modified in this fashion to create a physiologically advantageous stimulus.

In some implementations, the wireless stimulator device 114 may synthesize, from a stored PDM instance, a stimulation waveform for application at the electrodes. The stimulation waveform can be synthesized based on information in RF pulse received by the receiving dipole antenna(s) 238. In this implementation, the stimulator circuitry can synthesize the waveform using electrical energy solely from in the input signal. In this case, the RF pulse generator module 106 can directly control the envelope of the drive waveform within the wireless stimulator device 114, and thus no energy storage may be required inside the stimulator itself (e.g., in the form of a battery device) and the stimulator remains a passive device.

In some implementations, the drive waveform is single-phase drive waveform while in other implementations, the drive waveform may be multiphase drive. In the case of a single-phase drive waveform, for example, a negative-going rectangular pulse, this pulse comprises the physiological stimulus phase, and the charge-balance capacitor is polarized (charged) during this phase. After the drive pulse is completed, the charge balancing function is performed solely by the passive discharge of the charge-balance capacitor, where is dissipates its charge through the tissue in an opposite polarity relative to the preceding stimulus. In one implementation, a resistor within the stimulator facilitates the discharge of the charge-balance capacitor. In some implementations, using a passive discharge phase, the capacitor may allow virtually complete discharge prior to the onset of the subsequent stimulus pulse.

In the case of multiphase drive waveforms the wireless stimulator may perform internal switching to pass negative-going or positive-going pulses (phases) to the charge-balance capacitor. These pulses may be delivered in any sequence and with varying amplitudes and waveform shapes to achieve a desired physiological effect. For example, the stimulus phase may be followed by an actively driven charge-balancing phase, and/or the stimulus phase may be preceded by an opposite phase. Preceding the stimulus with an opposite-polarity phase, for example, can have the advantage of reducing the amplitude of the stimulus phase required to excite tissue.

In some implementations, the amplitude and timing of stimulus and charge-balancing phases is determined by the electrical energy and stimulation waveform information contained in the RF pulses from the RF pulse generator module 106. However, the synthesis of the stimulation waveforms is administered internally by circuitry onboard the wireless stimulator device 114, such as controller 250. During the onboard administration, data commands delivered from the pulse generator module 106 may contain the stimulation waveform information, for example, address information of a particular instance stored on the ROM device on wireless stimulator device 114.

Figure 3:
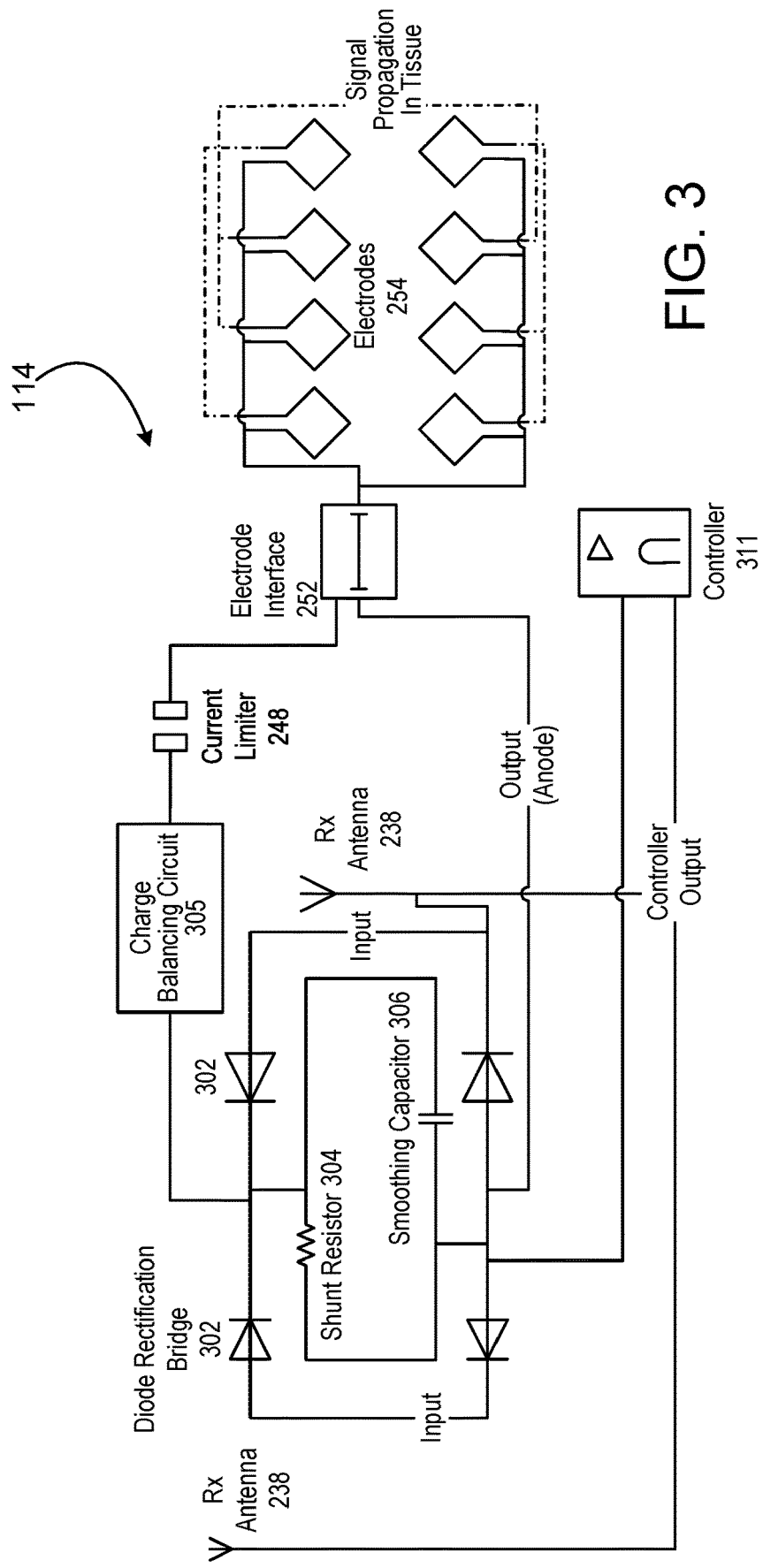
FIG. 3 shows an example of an implantable neural stimulator device of the wireless stimulation system.

Referring to FIG. 3, a circuit diagram is shown for an example of a wireless stimulator device 114. The example shown in FIG. 3 includes multiple electrode control and may employ full closed loop control. The wireless stimulation device includes an electrode array 254 in which the polarity of the electrodes can be assigned as cathodic or anodic, and for which the electrodes can be alternatively not powered with any energy. When energized, the charged electrodes create a volume conduction field of current density within the tissue. In this implementation, the wireless energy is received by the device through the dipole antenna(s) 238. The electrode array 254 is controlled through an on-board controller circuit 242 that sends the appropriate bit information to the electrode interface 252 in order to set the polarity of each electrode in the array, as well as power to each individual electrode. The lack of power to a specific electrode would set that electrode in a functional OFF position. In another implementation (not shown), the amount of current sent to each electrode is also controlled through the controller 242. The controller current, polarity and power state parameter data, shown as the controller output, is be sent back to the antenna(s) 238 for telemetry transmission back to the pulse generator module 106. The controller 242 also includes the functionality of current monitoring and sets a bit register counter so that the status of total current drawn can be sent back to the pulse generator module 106.

At least four diodes can be connected together to form a full wave bridge rectifier 302 attached to the dipole antenna(s) 238. Each diode, up to 100 micrometers in length, uses a junction potential to prevent the flow of negative electrical current, from cathode to anode, from passing through the device when said current does not exceed the reverse threshold. For neural stimulation via wireless power, transmitted through tissue, the natural inefficiency of the lossy material may lead to a low threshold voltage. In this implementation, a zero biased diode rectifier results in a low output impedance for the device. A resistor 304 and a smoothing capacitor 406 are placed across the output nodes of the bridge rectifier to discharge the electrodes to the ground of the bridge anode. The rectification bridge 302 may include two branches of diode pairs connecting an anode-to-anode and then cathode to cathode. The electrode polarity outputs, both cathode 308 and anode 310 are connected to the outputs formed by the bridge connection. Charge balancing circuitry 246 and current limiting circuitry 248 are placed in series with the outputs.

Figure 4:
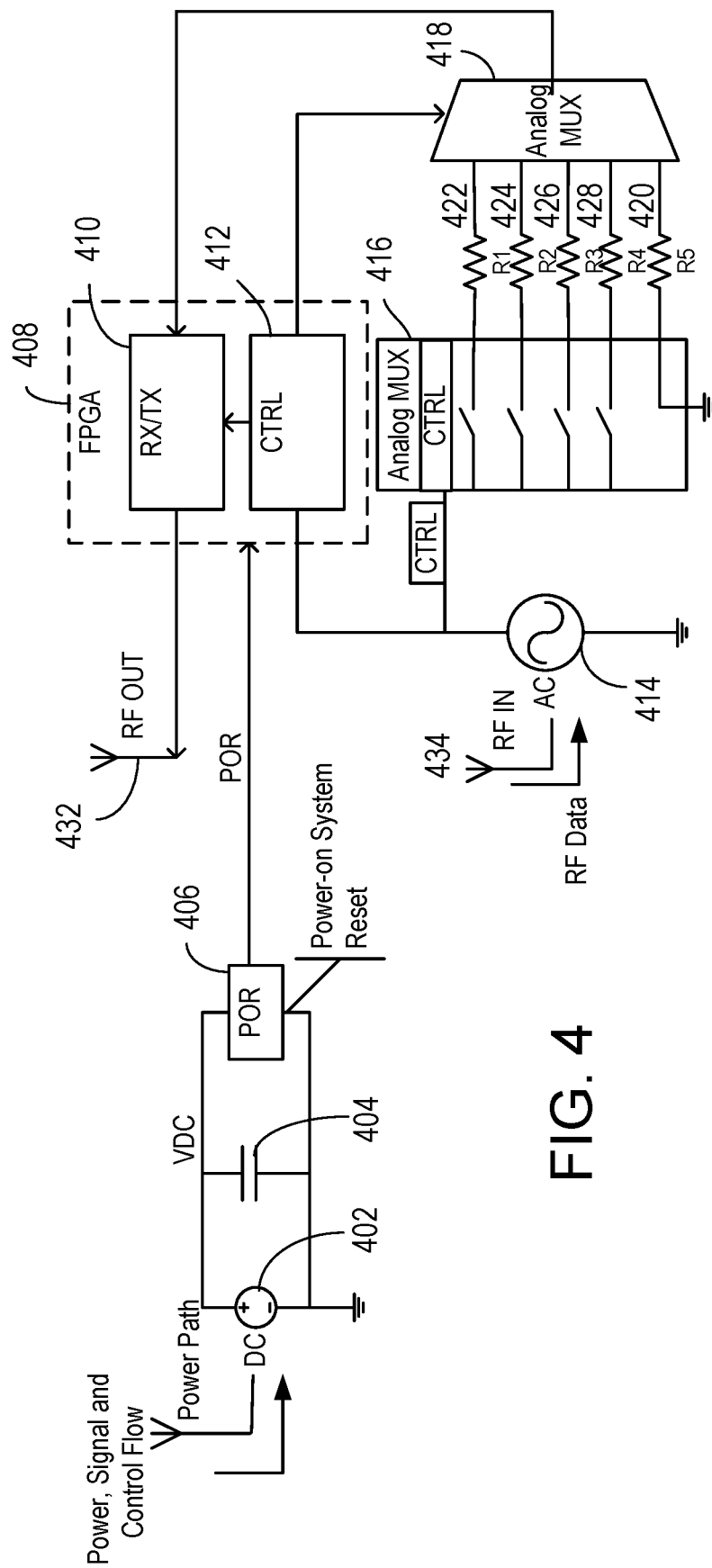
FIG. 4 shows an example of more details of the example of the wireless implantable stimulator device.

FIG. 4 is a schematic of an example of wireless stimulator device 114. A DC source 402 obtains energy from the transmission signal received at the wireless stimulator device 114 during the initial power-on portion of the transmission signal while the RF power is ramping up. In one implementation, a rectifier may rectify the received power-on portion to generate the DC source 402 and a capacitor 404 may store a charge from the rectified signal during the initial portion. When the stored charge reaches a certain voltage (for example, one sufficient or close to sufficient to power operations of the wireless stimulator device 114), the power-on reset circuit 406 may be triggered to send a power-on reset signal to reset components of the neural stimulator. The power-on set signal may be sent to circuit 408 to reset, for example, digital registers, digital switches, digital logic, or other digital components, such as transmit and receive logic 410. The digital components may also be associated with a control module 412. For example, a control module 412 may include electrode control 252, register file, etc. The power-on reset may reset the digital logic so that the circuit 408 begins operating from a known, initial state.

In some implementations, the power-on reset signal may subsequently cause the FPGA circuit 408 to transmit a power-on reset telemetry signal back to MFS to indicate that the implantable wireless stimulator device 114 is ready to receive the configuration portion of the transmission signal that contains the polarity assignment information. For example, the control module 412 may signal the RX/TX module 410 to send the power-on reset telemetry signal to the telemetry antenna 432 for transmission to MFS.

In other implementations, the power-on reset telemetry signal may not be provided. As discussed above, due to the proximity between MFS and implantable, passive stimulator device 114, signal degradation due to propagation loss may not be severe enough to warrant implementations of handshake signals from the implantable, passive stimulator device 114 in response to the transmission signal. In addition, the operational efficiency of implantable, passive neural stimulator device 114 may be another factor that weighs against implementing handshake signals.

Once the FPGA circuit 408 has been reset to an initial state, the FPGA circuit 408 transitions to a configuration mode configured to read polarity assignments encoded on the received transmission signal during the configuration state. In some implementations, the configuration portion of the transmission signal may arrive at the wireless stimulation device through the RX antenna 434. The transmission signal received may provide an AC source 414. The AC source 414 may be at the carrier frequency of the transmission signal, for example, from about 300 MHz to about 8 GHz.

Thereafter, the control module 412 may read the polarity assignment information and set the polarity for each electrode through the analog mux control 416 according to the polarity assignment information in the configuration portion of the received transmission signal. The electrode interface 252 may be one example of analog mux control 416, which may provide a channel to a respective electrode of the implantable wireless stimulator device.

Once the polarity for each electrode is set through the analog mux control 416, the implantable wireless stimulator device is ready to receive the stimulation waveforms. Some implementations may not employ a handshake signal to indicate the wireless stimulator device is ready to receive the stimulation waveforms. Rather, the transmission signal may automatically transition from the configuration portion to the stimulation portion. In other implementations, the implantable wireless stimulator device may provide a handshake signal to inform the MFS that implantable wireless stimulator device 114 is ready to receive the stimulation portion of the transmission signal. The handshake signal, if implemented, may be provided by RX/TX module 410 and transmitted by telemetry antenna 432.

In some implementations, the stimulation portion of the transmission signal may also arrive at implantable wireless stimulation device through the RX antenna 434. The transmission signal received may provide an AC source 414. The AC source 414 may be at the carrier frequency of the transmission signal, for example, from about 300 MHz to about 8 GHz. The stimulation portion may be rectified and conditioned in accordance with discussions above to provide an extracted stimulation waveform. The extracted stimulation waveform may be applied to each electrode of the implantable wireless stimulator device. In some embodiments, the application of the stimulation waveform may be concurrent, i.e., applied to the electrodes all at once. As discussed above, the polarity of each electrode has already been set and the stimulation waveform has been applied to the electrodes in accordance with the polarity settings for the corresponding channel.

In some implementations, each channel of analog mux control 416 is connected to a corresponding electrode and may have a reference resistor placed serially. For example, FIG. 4 shows reference resistors 422, 424, 426, and 428 in a serial connection with a matching channel. Analog mux control 416 may additionally include a calibration resistor 420 placed in a separate and grounded channel. The calibration resistor 420 is in parallel with a given electrode on a particular channel. The reference resistors 422, 424, 426, and 428 as well as the calibration resistor 420 may also be known as sensing resistors.

In some configurations, an analog controlled carrier modulator may receive a differential voltage that is used to determine the carrier frequency that should be generated. The generated carrier frequency may be proportional to the differential voltage. An example analog controlled carrier modulator is VCO.

In one configuration, the carrier frequency may indicate an absolute voltage, measured in terms of the relative difference from a pre-determined and known voltage. For example, the differential voltage may be the difference between a voltage across a reference resistor connected to a channel under measurement and a standard voltage. The differential voltage may be the difference between a voltage across calibration resistor 420 and the standard voltage. One example standard voltage may be the ground.

In another configuration, the carrier frequency may reveal an impedance characteristic of a given channel. For example, the differential voltage may be the difference between the voltage at the electrode connected to the channel under measurement and a voltage across the reference resistor in series. Because of the serial connection, a comparison of the voltage across the reference resistor and the voltage at the electrode would indicate the impedance of the underlying tissue being stimulated relative to the impedance of the reference resistor. As the reference resistor's impedance is known, the impedance of the underlying tissue being stimulated may be inferred based on the resulting carrier frequency.

For example, the differential voltage may be the difference between a voltage at the calibration resistor and a voltage across the reference resistor. Because the calibration resistor is placed in parallel to a given channel, the voltage at the calibration is substantially the same as the voltage at the given channel. Because the reference resistor is in a serial connection with the given channel, the voltage at the reference resistor is a part of the voltage across the given channel. Thus, the difference between the voltage at the calibration resistor and the voltage across the reference resistor correspond to the voltage drop at the electrode. Hence, the voltage at the electrode may be inferred based on the voltage difference.

In yet another configuration, the carrier frequency may provide a reading of a current. For example, if the voltage over reference resistor 422 has been measured, as discussed above, the current going through reference resistor and the corresponding channel may be inferred by dividing the measured voltage by the impedance of reference resistor 422.

Many variations may exist in accordance with the specifically disclosed examples above. The examples and their variations may sense one or more electrical parameters concurrently and may use the concurrently sensed electrical parameters to drive an analog controlled modulator device. The resulting carrier frequency varies with the differential of the concurrent measurements. The telemetry feedback signal may include a signal at the resulting carrier frequency.

The MFS may determine the carrier frequency variation by demodulating at a fixed frequency and measure phase shift accumulation caused by the carrier frequency variation. Generally, a few cycles of RF waves at the resulting carrier frequency may be sufficient to resolve the underlying carrier frequency variation. The determined variation may indicate an operation characteristic of the implantable wireless stimulator device 114. The operation characteristics may include an impedance, a power, a voltage, a current, etc. The operation characteristics may be associated with an individual channel. Therefore, the sensing and carrier frequency modulation may be channel specific and applied to one channel at a given time. Consequently, the telemetry feedback signal may be time shared by the various channels of the implantable wireless stimulator device 114.

In one configuration, the analog MUX 418 may be used by the controller module 412 to select a particular channel in a time-sharing scheme. The sensed information for the particular channel, for example, in the form of a carrier frequency modulation, may be routed to RX/TX module 410. Thereafter, RX/TX module 410 transmits, through the telemetry antenna 432, to the MFS, the telemetry feedback encoding the sensed information for the particular channel.

Some implementations may include an application-specific integrated circuit (ASIC) chip on the wireless stimulator device for processing input signal and interfacing with the implanted electrodes. The ASIC chip may be coupled to antenna(s) to receive the input signal from an external controller. The ASIC chip may harvest RF power from the received input signal to power the ASIC chip and the electrodes. The ASIC chip may also extract polarity setting information from the received input signal and use such information to set the polarity for electrode interfaces. Moreover, the ASIC chip may extract waveform parameters from the received input signal and use such information to create electrical impulses for stimulating excitable tissues through the electrodes. A pulse-density modulation may be utilized to synthesize stimulation waveforms suitable for stimulating neural tissue. In some instances, an arbitrary waveform shape is created regardless of the underlying tissue characteristics. In these instances, the arbitrary waveform shape is created consistently in a repeatable manner by leveraging the low-pass spectral characteristic of analog circuits driving the electrodes as well as capacitive nature of tissue impedance. In one example, the stimulation waveform is constructed based on a single-bit representation that encodes the amplitude information. In this example, the amplitude information may be encoded in the lower spectral region. In addition, the ASIC chip may include a current steering feature to mirror currents to each electrode with evenness while maintaining a compact chip size.

Figure 5:
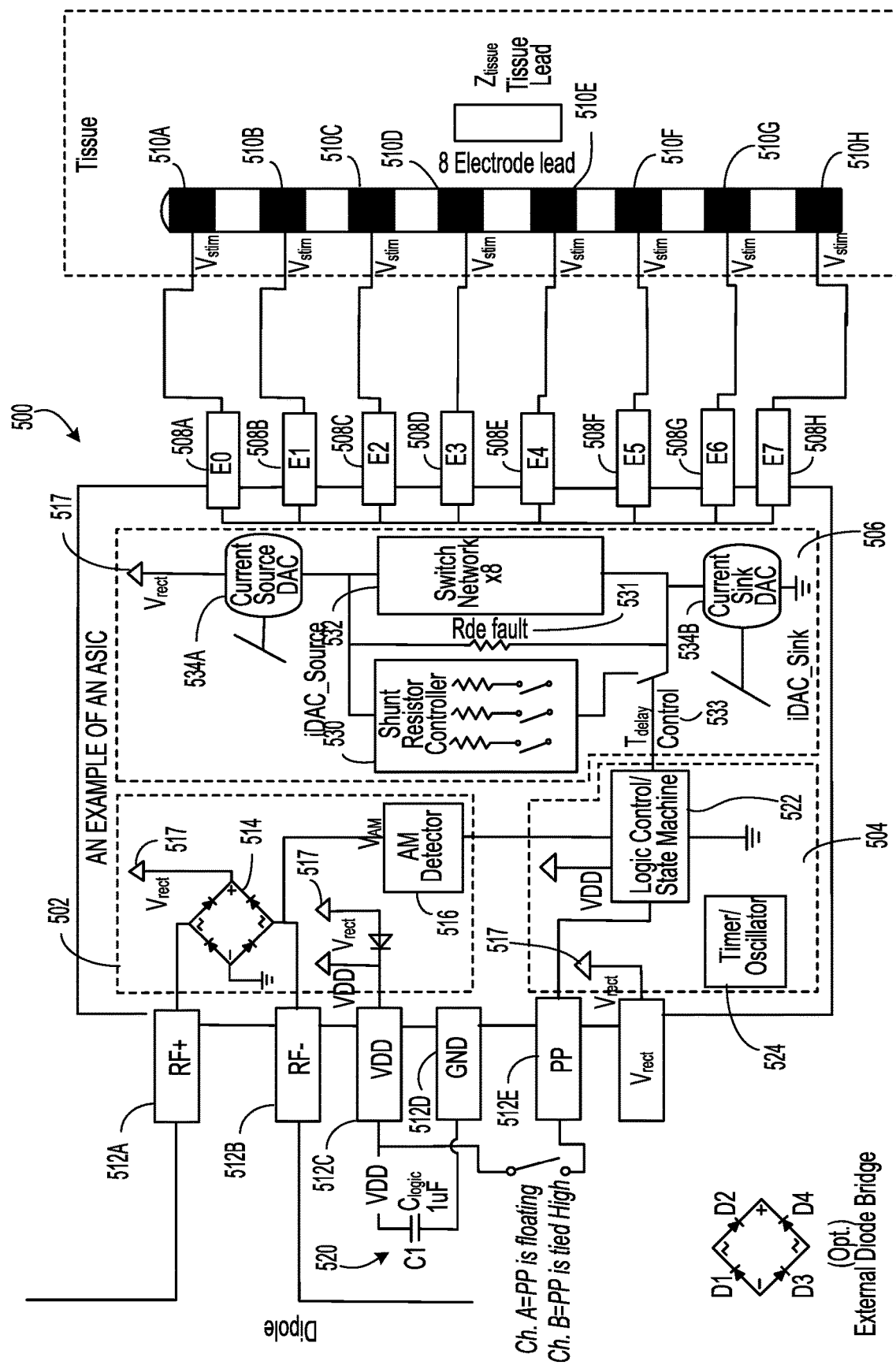
FIG. 5 shows an example of an ASIC on the wireless implantable stimulator device.

FIG. 5 is a diagram of an example of ASIC chip 500 for implantable use. Chip 500 may be fabricated based on a 0.6 um, double poly process utilizing High Value resistors, Schottky diodes and High Voltage Transistors. In some implementations, chip 500 can be fabricated at a width of 0.5 mm for fitting into, for example, an 18 Gauge needle. In these implementations, chip 500 can have a length-width ratio of up to 10 to 1. Chip 500 can be coupled to, for example, either four (4) or eight (8) platinum-iridium electrodes that deliver electrical impulses to tissue.

Chip 500 includes RF to DC rectifying circuit 502, a logic control circuit 504, and a driving circuit 506. RF to DC rectifying circuit 502 is coupled to differential antennas 512A and 512B. An RF input signal can be received at the differential antennas and then rectified to have the amplitude detected. The rectified signal may provide power for the chip 500. Thereafter, logic control circuit 504 may extract waveform parameters from the amplitude detected signal. Subsequently, logic control circuit 504 may generate electrical impulses according to the extracted waveform parameters and solely based on the extracted electric power. The generated electrical impulses may then be provided to the driving circuit 506, which includes charge balancing and current mirroring circuits. Driving circuit 506 is coupled to electrode interfaces 508A to 508H, each coupled to a respective electrical load 509A through 509H. The electrical impulses are subsequently delivered to each electrode, namely 510A through 510H.

In this diagram, a diode bridge circuit 514 is included to provide full-wave rectification to the input signal received in differential form from differential antennas 512A and 512B. Full-wave rectification may utilize both the positive and negative portions of the RF input signal as received at differential antennas 512A and 512B.

In some implementations, a dipole antenna in a differential configuration may be embedded into a wireless implantable stimulator device. The dipole antenna receives power, serial communication, and stimulus waveforms from an external transmitter placed outside the patient's body. The dipole antenna is connected directly to a flexible circuit board embedded within the implantable stimulator device that contains discrete components and chip 500. Chip 500 can include wireless serial command receiver with up to eight channel multiplexing functionality.

The rectification may provide power to remaining portions of chip 500. In some instances, VDD circuit 518 and ground circuit 519 are coupled to capacitor C1 520 to provide stored charges. The stored charges may generally power chip 500. In some implementations, a diode may be used to supply the VDD logic supply from Vrect. If chip 500 is active and the voltage VDD dips below 1.8V, chip 500 may enter into a "VDD low voltage recovery" mode. In this state any/all high side drivers will be temporarily overridden to high impedance state (Hi-Z) and all low side drivers will be Hi-Z. Once VDD returns t6 above 3.0V state and in the running mode the drivers would return to their previously programmed state.

Output from rectifying circuit 502 is coupled to the logic control circuit 504. As depicted, logic control circuit 504 may include logic control/state machine 522 and timer/oscillator 524. Logic control/state machine 522 may be coupled to channel selector 526.

The received RF input signal may contain waveform parameters for electrical impulses to stimulate tissues. The received RF input signal may contain polarity setting information for setting the interface for each electrode.

In some implementations, AM detector 516 may output logic zero when RF power is received. In some implementations, pre-amplification of low voltage data signals or limiting of high voltage data signals may extend the operational range of the AM detector 516. As such, signals 100 mV or greater will be detected. AM detector 516 may decode serial streams that are transmitted at 19200 Baud. The AM detector 516 input may be internal to chip 500 and characterized for use at high frequencies (869-915 MHz).

AM detector 516 may generally process rectified signals within a nominal range from between 50 mVpp to 15 Vpp power supply levels (peak to peak). AM detector 516 may include a preamp to clamp higher swing signals without output collapsing or folding down. The preamp should have sufficient gain and low offset to resolve 100 m Vpp data signals.

AM detector 516 may detect serial data encoded using IrDA (Infrared Data Association) formatting in, for example, SIR. The serial data receiver may be included in AM detector 516 and may convert the data from a serial format into a parallel format. Operations of the serial data receiver hardware may be controlled by a clock signal, which runs at a multiple of the data rate. In some implementations, the receiver can test the state of the incoming signal on each clock pulse to search the start bit. If the apparent start bit is valid, then the bit signals the start of a new character. If not, the bit is considered a spurious pulse or power pulse and is ignored. After waiting a further bit time, the state of the line is again sampled and the resulting level clocked into a shift register.

After the required number of bit periods for the character length have elapsed, the contents of the shift register are made available to the receiving system. The serial data receiver has no shared timing system with the transmitter apart from the communication signal.

Serial data receiver on chip 500 may receive and buffer seven (7) eight-bit words. The data contained in the words may be used to program the control registers in the receiver IC LMI927 if a checksum match is successful. The data will be ignored if a checksum match is unsuccessful and the receiver will continue to listen for valid data. The serial data receiver will reset and prepare to receive a new word if a received byte does not meet IrDA (SIR) framing parameters. This will allow the serial receiver to quickly reset after being falsely activated by reception of a spurious signal or a stim power pulse. The serial data receiver will not have to wait to fully receive all words if any individual byte does not meet timing parameters.

Chip 500 may remain in an un-configured state (all high-side outputs are high-Z, low-side outputs are in triode mode) until a valid set of serial data is received. Notably, in some implementations, the serial receiver may be not operational if the Device Lock bit is set.

Logic control/state machine 522 may be synchronized by timer/oscillator 524. The synchronization may enable logic control/state machine 522 to extract and decode waveform parameters as well as polarity setting information. Logic control/state machine 522 may then create one or more electrical impulses according to the waveform parameters. The Logic control/state machine 522 may also set polarities of electrode interfaces 508A to 508H according to the extracted polarity setting information.

The output of Logic Control/State Machine 522 may be coupled to driving circuit 506 which includes features of charge balancing, shunt resistors, and current mirroring. In particular, driving circuit 506 includes shunt resistor controller 530 constructed to couple a shunt resistor to switch network 532. The coupling can enhance default resistor 531 through delay controller 533. The delay controller may insert a corresponding shunt resistor to the circuit including the stimulating electrode at the end of an electrical impulse to reduce the amount of leakage current.

As disclosed, the PDM signal, as stored in a ROM, can be serially shifted out so that the PDM signal is played to switch network and a stimulation waveform suitable for stimulating neuro tissue is applied at a particular electrode. The amplitude of the synthesized stimulation waveform can be determined by the power supply level, which depends on the electromagnetic energy contained in the input signal. While the switch network and various drive circuits form analog low-pass filters that are integrative and facilitate the reconstruction of the desire stimulation waveform, the tissue impedance is low-pass in characteristic and capacitive in nature, which also aids in the reconstruction of the desired stimulation waveform.

In some implementations, the stimulating electrical impulse is delivered to a particular electrode through switch network 532. To deliver electrical impulses at both polarities, the switch network is coupled to current source DAC 534A and current sink DAC 534B. As depicted, current source DAC 534A includes a binary interface coupled to the rectifying voltage Vrect 517. This binary interface represents a form of a single-bit interface to deliver either a high or low current. Current source DAC 534A is invoked with the polarity of the connected electrode set as positive. Similarly, current sink DAC 534B includes a binary interface (also as a form of a single-bit interface to deliver either a high or low current). Current sink DAC 534B is invoked with the polarity of the connected electrode set as negative.

Current source DAC 534A and current sink DAC 534B are complementary so that a charge balanced discharge pattern can be advantageously generated at the electrodes. In some instances, current source DAC 534A and current sink DAC 534B both include current mirrors that can function to reproduce a copy of the current in one device (for example, the device that generates voltage Vrect 517) by replicating the current in another device (for example, current source DAC 534A or current sink DAC 534B). A current mirror generally has a relatively high output resistance can facilitate a constant output current regardless of load conditions. Another feature of the current mirror is a relatively low input resistance that is advantageous for maintaining the input current constant regardless of drive conditions.

While current source DAC 534A and current sink 534B include binary interfaces, the stimulation waveforms can be synthesized to have an arbitrary shape in the amplitude. Although conventional wisdom may lead to a design choice of a multi-bit DAC to handle, for example, a rail-to-rail operation in which each bit may lead to a 6 dB dynamic range, hardware requirements associated with multi-bit data storage and multi-bit DACs is quite high. Some implementations can leverage the low-pass spectral characteristic of the single-bit interface, including analog driving circuits. In particular, the single-bit interface includes analog components that form a current buffer. These analog components generally favor lower frequency components and exhibit a low-pass frequency operating characteristic. Moreover, the coupling tissue can introduce filtering capacitance that facilitates the reconstruction of a stimulation waveform of arbitrary shape (e.g., a charge balanced waveform).

Chip 500 may include a supervisory Power On Reset (POR) circuit designed to keep the device in reset until the system voltage has reached the proper level and stabilized. The POR circuit also operates as protection from brownout conditions when the supply voltage drops below a minimum operating level. The POR circuit design is such that it incorporates appropriate hysteresis between reset and enable levels to prevent start up inrush currents from causing the device to reset during normal operating power-up conditions. The POR circuit performs as needed to maintain proper chip functionality under all power fluctuation conditions including high-speed transients and slow rate of change voltage conditions. If required, the POR circuit can incorporate a watchdog timer tick event to ensure proper operation of the chip 500.

A number of implementations have been described. Nevertheless, it will be understood that various modifications may be made. Accordingly, other implementations are within the scope of the following claims.

What is claimed is:

1. A method to synthesize a stimulus waveform, the method comprising:
 receiving, by one or more antennas of an implantable stimulation device and from an external module, an input signal through non-inductive coupling;
 rectifying the input signal, the input signal containing
  (i) electrical energy to operate the implantable stimulation device, and
  (ii) configuration data including parameters for generating a specific stimulus waveform;
 extracting the electrical energy and the configuration data from the rectified input signal; and
 based on the parameters in the configuration data,
  (i) selecting a digital representation of a pulse density modulation (PDM) encoded stimulus waveform signal from a memory device of a circuit of the implantable stimulation device, wherein the circuit is coupled to the one or more antennas and includes (i) the memory device that stores the digital representation of the PDM encoded stimulus waveform for generating the specific stimulus waveform, (ii) a clock, (iii) an oscillator device, and (iv) one or more electrode drivers that comprise at least an H bridge electrode driver, (ii) controlling the oscillator device of the implantable stimulation device to signal the clock to clock the PDM encoded stimulus waveform signal and convert the digital representation of the PDM encoded stimulus waveform signal using the extracted electrical energy into the specific stimulus waveform, and (iii) generating the specific stimulus waveform with the one or more electrode drivers of the implantable stimulation device.

2. The method of claim 1, further comprising:
applying the specific stimulus waveform at one or more electrodes of the implantable stimulation device, wherein the one or more electrodes are coupled to the circuit.

3. The method of claim 1, further comprising:
tuning the PDM encoded stimulus waveform signal to treat a particular condition for a subject.

4. The method of claim 1, further comprising:
pre-loading the PDM encoded stimulus waveform signal as a bit stream such that the specific stimulus waveform is generated at least in part by using the oscillator device and the clock to serially shift out the bit stream.

5. An implantable stimulation device receiving instructions from an external module and configured to perform operations comprising:
receiving, by one or more antennas of the implantable stimulation device and from the external module, an input signal through non-inductive coupling;
rectifying the input signal, the input signal containing
(i) electrical energy to operate the implantable stimulation device, and
(ii) configuration data including parameters for generating a specific stimulus waveform;
extracting the electrical energy and the configuration data from the rectified input signal; and
based on the parameters in the configuration data,
(i) selecting a digital representation of a pulse density modulation (PDM) encoded stimulus waveform signal from a memory device of a circuit of the implantable stimulation device, wherein the circuit is coupled to the one or more antennas and includes (i) the memory device that stores the digital representation of the PDM encoded stimulus waveform for generating the specific stimulus waveform, (ii) a clock, (iii) an oscillator device, and (iv) one or more electrode drivers that comprise at least an H bridge electrode driver, (ii) controlling the oscillator device of the implantable stimulation device to signal the clock to clock the PDM encoded stimulus waveform signal and convert the digital representation of the PDM encoded stimulus waveform signal using the extracted electrical energy into the specific stimulus waveform, and (iii) generating the specific stimulus waveform with the one or more electrode drivers of the implantable stimulation device.

6. The implantable stimulation device of claim 5, wherein the operations further comprise:
applying the specific stimulus waveform at one or more electrodes of the implantable stimulation device, wherein the one or more electrodes are coupled to the circuit.

7. The implantable stimulation device of claim 5, further comprising:
tuning the PDM encoded stimulus waveform signal to treat a particular condition for a subject.

8. The implantable stimulation device of claim 5, further comprising:
pre-loading the PDM encoded stimulus waveform signal as a bit stream such that the specific stimulus waveform is generated at least in part by using the oscillator device and the clock to serially shift out the bit stream.

9. The implantable stimulation device of claim 5, wherein the memory of the circuit stores digital representations of more than one PDM encoded stimulus waveform signals.

* * * * *

UNITED STATES PATENT AND TRADEMARK OFFICE
CERTIFICATE OF CORRECTION

PATENT NO. : 11,672,488 B1
APPLICATION NO. : 16/855252
DATED : June 13, 2023
INVENTOR(S) : Laura Tyler Perryman, Bertan Bakkaloglu and Chad David Andresen It is certified that error appears in the above-identified patent and that said Letters Patent is hereby corrected as shown below:

On the Title Page

Column 1, item (73) Assignee, delete "Stimwave Technologies Incorporated" and insert --Curonix LLC--, therefor.

Signed and Sealed this
Third Day of September, 2024

Katherine Kelly Vidal
*Director of the United States Patent and Trademark Office*